US008467615B2

(12) United States Patent
Hirakawa

(10) Patent No.: US 8,467,615 B2
(45) Date of Patent: Jun. 18, 2013

(54) IMAGE DISPLAY APPARATUS

(75) Inventor: Katsumi Hirakawa, Tokyo (JP)

(73) Assignee: Olympus Corporation, Tokyo (JP)

( * ) Notice: Subject to any disclaimer, the term of this patent is extended or adjusted under 35 U.S.C. 154(b) by 1901 days.

(21) Appl. No.: 11/631,068

(22) PCT Filed: Nov. 17, 2005

(86) PCT No.: PCT/JP2005/021142
§ 371 (c)(1),
(2), (4) Date: Dec. 28, 2006

(87) PCT Pub. No.: WO2006/057193
PCT Pub. Date: Jun. 1, 2006

(65) Prior Publication Data
US 2008/0024599 A1 Jan. 31, 2008

(30) Foreign Application Priority Data

Nov. 29, 2004 (JP) .................................. 2004-344954

(51) Int. Cl.
*G06K 9/36* (2006.01)
(52) U.S. Cl.
USPC ......... 382/232; 382/239; 348/207.1; 600/109
(58) Field of Classification Search
USPC ............... 348/207.1, 143–155; 382/232, 233, 382/239, 240, 250; 600/103, 109, 437, 442, 600/443, 459, 587
See application file for complete search history.

(56) References Cited

U.S. PATENT DOCUMENTS

| 6,350,238 | B1 * | 2/2002 | Olstad et al. ................... 600/437 |
| 6,709,387 | B1 * | 3/2004 | Glukhovsky et al. .......... 600/109 |
| 7,050,096 | B2 * | 5/2006 | Porter et al. ............. 348/231.99 |
| 7,242,852 | B2 * | 7/2007 | Sawada .......................... 386/295 |
| 7,274,389 | B1 * | 9/2007 | Hieda ......................... 348/207.1 |
| 7,486,981 | B2 * | 2/2009 | Davidson ...................... 600/407 |
| 7,557,833 | B2 * | 7/2009 | Okawa ........................ 348/220.1 |
| 7,773,123 | B2 * | 8/2010 | Kaneko et al. ............. 348/222.1 |
| 8,159,549 | B2 * | 4/2012 | Glukhovsky et al. ....... 348/222.1 |
| 8,164,672 | B2 * | 4/2012 | Meron et al. ............. 348/333.05 |
| 8,206,285 | B2 * | 6/2012 | Blijevsky ....................... 600/117 |
| 2001/0051766 | A1 * | 12/2001 | Gazdzinski .................. 600/309 |
| 2003/0023150 | A1 * | 1/2003 | Yokoi et al. .................... 600/300 |

(Continued)

FOREIGN PATENT DOCUMENTS

JP 08/110849 4/1996
JP 11-203845 7/1999

(Continued)

*Primary Examiner* — Lashonda Jacobs
(74) *Attorney, Agent, or Firm* — Scully, Scott, Murphy & Presser, P.C.

(57) ABSTRACT

An image display apparatus that can shorten time for observing a series of images of an interior of a subject without hampering observation of a desired region of interest is provided. The image display apparatus according to the present invention is an image display apparatus for displaying the series of images of the interior of the subject picked up at time series, including an image extracting unit 15a that extracts images each having a feature of a desired region in the interior of the subject and that identifies the extracted images as images of the desired region among the series of images, and a frame rate controller 15b that sets a display frame rate for the identified images of the desired region to be different from a display frame rate for images of regions other than the desired region.

18 Claims, 18 Drawing Sheets

U.S. PATENT DOCUMENTS

| | | | |
|---|---|---|---|
| 2003/0055317 A1* | 3/2003 | Taniguchi et al. | 600/117 |
| 2003/0151661 A1 | 8/2003 | Davidson et al. | |
| 2003/0181788 A1* | 9/2003 | Yokoi et al. | 600/160 |
| 2004/0062442 A1* | 4/2004 | Laumeyer et al. | 382/190 |
| 2006/0004255 A1* | 1/2006 | Iddan et al. | 600/160 |
| 2006/0115165 A1* | 6/2006 | Chao et al. | 382/239 |
| 2007/0118017 A1* | 5/2007 | Honda | 600/160 |
| 2007/0173714 A1* | 7/2007 | Hirakawa | 600/407 |
| 2008/0125627 A1* | 5/2008 | Mizuno | 600/109 |

FOREIGN PATENT DOCUMENTS

| | | |
|---|---|---|
| JP | 2004-154176 | 6/2004 |
| JP | 2004-521662 | 7/2004 |
| JP | 2004-321603 | 11/2004 |
| JP | 2004-321796 | 11/2004 |
| JP | 2005-518160 | 6/2005 |
| WO | WO 01/87377 A2 | 11/2001 |
| WO | WO 03/069913 A1 | 8/2003 |

* cited by examiner

DG3 NORMAL SETTING
DG4 SLOW SETTING
DG5 NORMAL SETTING

IMAGE DISPLAY APPARATUS

TECHNICAL FIELD

The present invention relates to an image display apparatus that displays a series of images of a desired subject picked up at time series.

BACKGROUND ART

In recent years, a capsule endoscope that is a swallowable endoscope including an imaging function and a radio communication function has appeared, and a capsule endoscope system that acquires image data on intra-subject images picked up by the capsule endoscope has been developed. In the capsule endoscope system, the capsule endoscope functions to move in the interior of the subject, i.e., interiors of organs such as the stomach and the small intestine according to their peristaltic movements since being swallowed from a subject's mouth for observation (examination) until being naturally discharged from the interior of the subject, and to pick up the intra-subject images at predetermined intervals of, for example, at intervals of 0.5 second.

During movement of the capsule endoscope in the interior of the subject, image data on the images picked up by the capsule endoscope is sequentially transmitted to the outside by radio communication and received by a receiving apparatus through a receiving antenna provided outside of the capsule endoscope. The receiving apparatus can reconstruct the image data based on radio signals sequentially received through the receiving antenna and thereby acquire intra-subject image data by the capsule endoscope. The receiving apparatus sequentially stores the acquired image data in a memory. By carrying the receiving apparatus including a radio communication function and a memory function, the subject can act freely since swallowing the capsule endoscope until the capsule endoscope is naturally discharged. An examiner such as a doctor or a nurse then loads the image data stored in the memory of the receiving apparatus into an image display apparatus, and displays the intra-subject images based on the obtained image data, for example, images of an organ on a display. The examiner can diagnose the subject while observing the images of the organ or the like displayed on the display.

Generally, such an image display apparatus includes a processing function for sequentially displaying a series of images picked up by the capsule endoscope according to time series. For example, if an image of a to-be-observed region in the body of the subject is displayed, the examiner performs an operation for playing the image at slow rate so as to carefully observe the image. Furthermore, if an image of a region other than the to-be-observed image is displayed, the examiner performs an operation for playing the image at fast rate so as to shorten time for observing the series of intra-subject images. In relation to such a technique, there is known an image display apparatus that measures image similarity among sequentially displayed frames, that displays or cuts each image with high similarity at fast display frame rate by accelerating display frame rate if the obtained similarity is high, and that displays each image with low similarity at slow display frame rate by decelerating the display frame rate if the obtained similarity is low (see Patent Document 1).

Patent Document 1: U.S. Pat. No. 6,709,387

DISCLOSURE OF INVENTION

Problem to be Solved by the Invention

However, the image display apparatus described in the Patent Document displays or cuts each of the images high in similarity among the frames, irrespectively of the region in the subject displayed as the images picked up by the capsule endoscope. Accordingly, if the time for observing a series of intra-subject images is to be shortened, the conventional image display apparatus may possibly play images of a region which the examiner is interested in (a region of interest) such as a bleeding site or an examination target organ at fast rate or cut the images of the region of interest, with the result that a problem of making it difficult to observe the to-be-observed region of interest.

The present invention has been achieved in view of the above circumstances, and it is an object of the present invention to provide an image display apparatus capable of shortening time for observing a series of intra-subject images without hampering observation of a desired region of interest.

Means for Solving Problem

An image display apparatus according to the present invention for displaying a series of images of an interior of a subject picked up along time series, includes an image identifying unit that extracts images each having a feature of a desired region in the interior of the subject, and that identifies the extracted images among the series of images as images of the desired region; and a frame-rate controller that makes a display frame rate for the identified images of the desired region different from a display frame rate for images of regions other than the desired region.

In the image display apparatus according to the invention, the frame rate controller may make the display frame rate for the identified images of the desired region slower than the display frame rate for the images of the regions other than the desired region.

The image display apparatus according to the invention may further include an input unit that inputs an instruction for a display frame rate for the series of images, wherein the frame rate controller may set the display frame rate for which the instruction is input as a display frame rate for the series of images, may change the display frame rate for the images of the desired region among the set display frame rate to a rate slower than the set display frame rate, and may change the display frame rate for the images of the regions other than the desired region to a rate faster than the set display frame rate.

In the image display apparatus according to the invention, the frame rate controller may exclude images other than the identified images of the desired region among the series of images.

The image display apparatus according to the invention may further include a region selector that selects the desired region in the interior of the subject, wherein the image identifying unit may extract the images each having the feature of the selected desired region, and may identify the extracted images among the series of images as the images of the desired region.

In the image display apparatus according to the invention, the image identifying unit may further extract images each having a feature of a medically abnormal site, and may identify the extracted images among the identified images of the desired region as images of the abnormal site, and the frame rate controller may delete the images other than the images of the desired region among the series of images, and may make a display frame rate for the identified images of the abnormal site slower than the display frame rate for the images of the desired region except for the abnormal site.

In the image display apparatus according to the invention, the identified desired region may be one of an esophagus, a stomach, a small intestine, a large intestine, and a bleeding site in the interior of the subject.

Effect of the Invention

According to the present invention, it is advantageously possible to realize the image display apparatus that can automatically display the images of the desired region of interest at slow rate even if an operation for sequentially displaying a series of images at fast or standard display frame rate is performed, and that can shorten time for observing the series of images of the subject without hampering observation of the images of the desired region of interest.

EXPLANATIONS OF LETTERS OR NUMERALS

Figure 1:
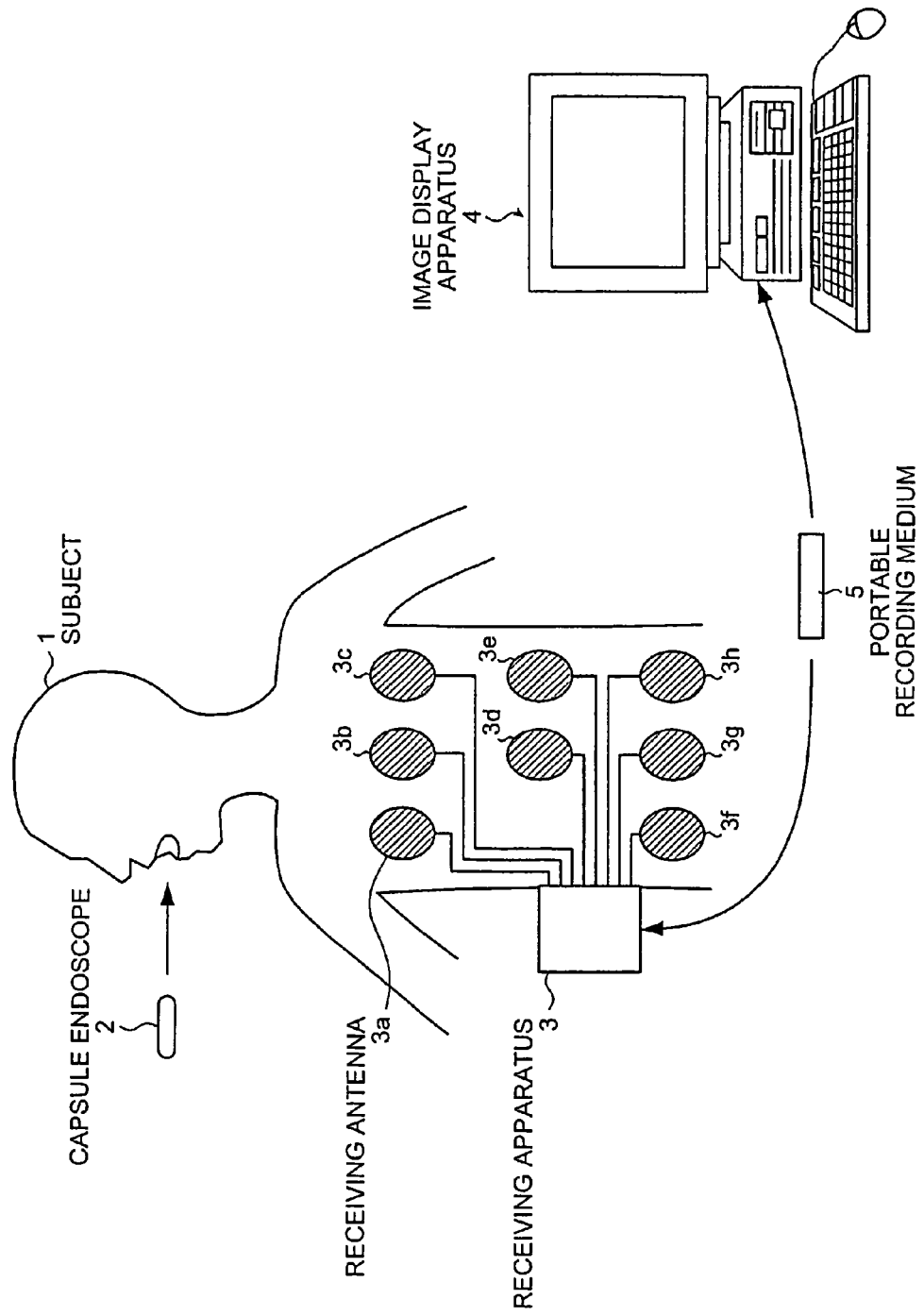
FIG. 1 a pattern diagram typically showing an example of a configuration of a capsule endoscope system using an image display apparatus according to a first embodiment of the present invention.

1 Subject
2 Capsule endoscope
3 Receiving apparatus
3a-3h Receiving antenna
4, 21, 31, 41 Image display apparatus
5 Portable recording medium
11 Input unit
12 Display unit
13 Reader-writer
14 Storage unit
15, 22, 32, 42 Control unit
15a, 22a, 32a, 42a Image extracting unit
15b, 32b, 42b Frame rate controller
22c Region selector
100 Play-operation icon group
101 PLAY icon
102 FRAME icon
103 FAST PLAY icon
104 REVERSE PLAY icon
105 PREVIOUS FRAME icon
106 FAST REVERSE icon
107 STOP icon
110 CLOSE icon
120 PLAY REGION SELECT icon
201 OK icon
202 CANCEL icon
A1 Main-image display area
A2 Subimage display area
B Scrollbar
Da, Db Image data
DG1-DG5 Image data group
K Cursor
S Slider
TS Timescale
W1 Window
W2 Window

BEST MODE(S) FOR CARRYING OUT THE INVENTION

Exemplary embodiments of an image display apparatus according to the present invention will be described hereinafter in detail with reference to the drawings. It is to be noted that the present invention is not limited by the embodiments.

First Embodiment

FIG. 1 is a pattern diagram typically showing an example of a configuration of a capsule endoscope system using an image display apparatus according to a first embodiment of the present invention. As shown in FIG. 1, the capsule endoscope system includes a capsule endoscope 2 that moves along a passing route in a body of a subject 1 and that picks up an image of an interior of the subject 1, a receiving apparatus 3 that receives image data transmitted from the capsule endoscope 2, an image display apparatus 4 that displays the image of the interior of the subject 1 picked up by the capsule endoscope 2, and a portable recording medium 5 that mediates between the receiving apparatus 3 and the image display apparatus 4 for transmitting and receiving information therebetween.

The capsule endoscope 2 includes an imaging function of imaging the interior of the subject 1 and a radio communication function of transmitting the image data obtained by imaging the interior of the subject 1 to the receiving apparatus 3. The capsule endoscope 2 passes through the esophagus in the body of the subject 1 and moves forward in body cavities by the peristaltic movement of a digestive lumen by being swallowed by the subject 1. At the same time, the capsule endoscope 2 sequentially picks up body cavity images of the subject 1 at predetermined intervals, e.g., at intervals of 0.5 second and sequentially transmits the obtained image data on the interior of the subject 1 to the receiving apparatus 3.

The receiving apparatus 3, to which receiving antennas 3a to 3h are connected, holds radio communication with the capsule endoscope 2 using the receiving antennas 3a to 3h. Specifically, the receiving apparatus 3 receives a radio signal from the capsule endoscope through one of the receiving antennas 3a to 3h, and acquires the image data on the interior of the subject 1 based on the received radio signal. Furthermore, the receiving apparatus 3, to which the portable recording medium 5 is detachably attached, sequentially stores the image data on the interior of the subject 1 sequentially acquired from the capsule endoscope 2 in the portable recording medium 5.

Each of the receiving antennas 3a to 3h, which is realized by using, for example, a loop antenna, receives the radio signal transmitted from the capsule endoscope 2. As shown in FIG. 1, the receiving antennas 3a to 3h are arranged at predetermined positions on the body surface of the subject 1, e.g., positions corresponding to the passing route of the capsule endoscope 2, respectively. Alternatively, the receiving antennas 3a to 3h can be arranged at predetermined positions on a jacket which the subject 1 wears, respectively. In this alternative, the receiving antennas 3a to 3h are arranged at the predetermined positions on the body surface to correspond to the passing route in the subject 1 of the capsule endoscope 2, respectively, by causing the subject 1 to wear this jacket. Furthermore, a plurality of receiving antennas can be arranged on the subject 1. In this case, the number of arranged receiving antennas is not limited particularly to eight.

The portable recording medium 5 is a portable recording media such as a compact flash (registered trademark) or a smart media. The portable recording medium 5 is structured to be detachable from the receiving apparatus 3 or the image display apparatus 4, and to be able to output and record information when being attached to the receiving apparatus 3 or the image display apparatus 4. Specifically, when being attached to the receiving apparatus 3, the portable recording medium 5 can sequentially store therein image data or the like acquired by the receiving apparatus 3 from the capsule endoscope 2. Moreover, after the capsule endoscope 2 is discharged from the subject 1, the portable recording medium 5 is detached from the receiving apparatus 3 and attached to the image display apparatus 4, and the stored image data or the like is loaded into the image display apparatus 4.

The image display apparatus 4, which is to display images or the like picked up by the capsule endoscope 2, is configured like a workstation or the like that displays the images based on the image data or the like obtained through the portable recording medium 5, e.g., images of the organs or the like in the body of the subject 1. Further, the image display apparatus 4 includes a processing function of causing an examiner such as a doctor or a nurse to diagnose the subject 1 based on the intra-subject images picked up by the capsule endoscope 2. The examiner can diagnose the subject 1 by causing the image display apparatus 4 to sequentially display the images of the interior of the subject 1 and observing (examining) a region of interest in the subject 1 based on the displayed images.

Figure 2:
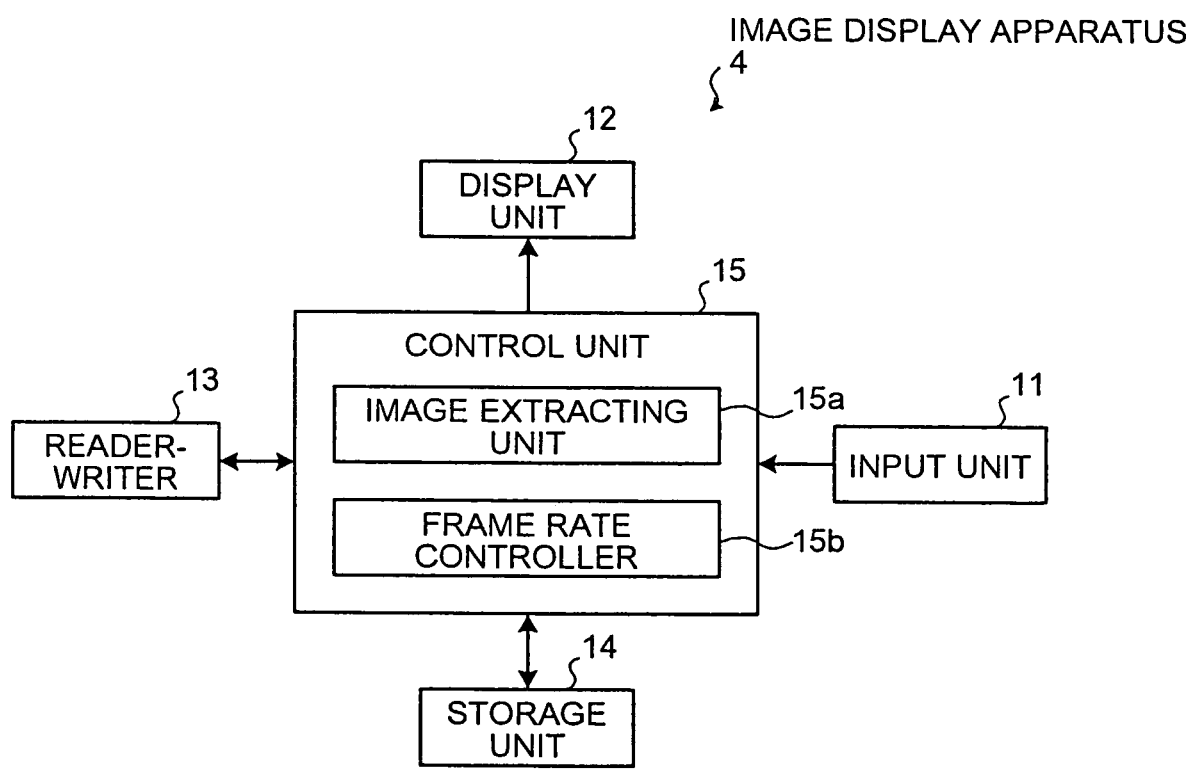
FIG. 2 is a block diagram typically showing an example of a configuration of the image display apparatus according to the first embodiment of the present invention.

FIG. 2 is a block diagram typically showing an example of a configuration of the image display apparatus 4. As shown in FIG. 2, the image display apparatus 4 includes an input unit 11 that inputs various information for displaying and observing the images picked up by the capsule endoscope 2, a display unit 12 that displays the various information such as the images of the interior of the subject 1 on a screen for observing (examining) the interior of the subject 1 and for diagnosing the subject 1, and a reader-writer 13 for loading the image data or the like stored in the portable recording medium 5. Moreover, the image display apparatus 4 includes a storage unit 14 that stores therein the various data such as the image data loaded from the portable recording medium 5 necessary for observing and diagnosing the subject 1, and a control unit 15 that exercises driving control over the respective constituent elements of the image display apparatus 4 and input/output control over the various information input/output put to/from the respective constituent elements, and performs an information processing.

The input unit 11, which is realized by using a pointing device such as a keyboard or a mouse or by a combination thereof, inputs instruction information for processings performed by the image display apparatus 4 and the various information on subject 1 to the control unit 15 according to an operator's input operation. For example, the input unit 11 inputs instruction information on an instruction to perform a processing for storing the image data loaded from the portable recording medium 5 in the storage unit 14, instruction information on an instruction to perform a processing for displaying the images of the interior of the subject 1 on the display unit 12, and patient information such as a name, a sex, a birth data or a patient ID of the subject 1, to the control unit 15.

The display unit 12, which is realized by using a display of various types such as a CRT display, a liquid crystal display, an organic EL display or a plasma display, displays the various information instructed to be displayed by the control unit 15. The display unit 12 displays, as various information for examining and diagnosing the subject 1, a series of images of the interior of the subject 1 picked up by the capsule endoscope 2 at time series at predetermined intervals, e.g., at intervals of 0.5 second, the patient information and the like.

The reader-writer 13, to which the portable recording medium 5 is detachably attached, mediates the image display apparatus 4 and the portable recording medium 5 attached to the reader-writer 13 for transmitting and receiving various data. Specifically, the reader-writer 13 loads information stored in the portable recording medium 5 attached to the reader-writer 13, e.g., the image data obtained by the capsule endoscope 2, and transfers the obtained image data or the like to the control unit 15. The reader-writer 13 also includes a function of recording input information from the control unit 15 to the portable recording medium 5 attached to the reader-writer 13, and a function of performing a format processing.

The storage unit 14 is realized by using an IC memory of various types such as a RAM or an EEPROM, a hard disk or the like. The storage unit 14 can be realized by a drive that is structured to detachably attach thereto an optical disk or a magnetooptical disk such as a CD (Compact Disk) or a DVD (Digital Versatile Disk) and that can read or write the image data or the like from or to the CD or DVD attached thereto. The storage unit 14 stores the various information such as the image data instructed to be stored by the control unit 15 in the storage unit 14 itself or in the disk of various types attached thereto. Furthermore, the control unit 14 reads the information stored therein and instructed to be read or the information stored in the disk of various types attached thereto, and transfers the read information to the control unit 15.

The control unit 15 is realized by using a CPU (Central Processing Unit) that executes various processing programs, a ROM in which the various processing programs or the like executed by the CPU are recorded in advance, and a RAM that temporarily stores therein various information such as operation parameters for the respective processings. The control unit 15 functions to control driving of the input unit 11, the display unit 12, the reader-writer 13, and the storage unit 14, to control input/output of information to/from the respective constituent elements, and to cause the respective constituent elements to perform an information processing for inputting/outputting the various information.

The control unit 15 includes an image extracting unit 15a and a frame rate controller 15b. The image extracting unit 15a extracts image data having a feature of the region of interest in the subject 1 from a series of image data on the subject 1, and identifies the extracted image data as image data on the region of interest for which an image is to be displayed on the display unit 12 at slow display frame rate so that the examiner can observe the region of interest. Namely, the image extracting unit 15a functions as an image identifying unit that identifies the image data on the region of interest among the series of image data picked up by the capsule endoscope 2. It is to be noted that this region of interest is a region in which the examiner is interested when observing (examining) the subject 1, e.g., a bleeding site in the subject 1. The image extracting unit 15a calculates feature data on each pixel that constitutes the image data, detects whether red elements are present and distributed using the obtained feature data, and determines whether an imaged region of the image data is the bleeding site based on a detection result about the red elements. The image extracting unit 15a extracts the image data the imaged region of which is the bleeding site, i.e., the image data including the read elements or a color distribution characteristic of the bleeding site, as the image data on the region of interest. The frame rate controller 15b controls display frame rates for images displayed on the display unit 12. The control unit 15 controls the display unit 12 to sequentially display the images at the display frame rates set by the frame rate controller 15b.

Figure 3:
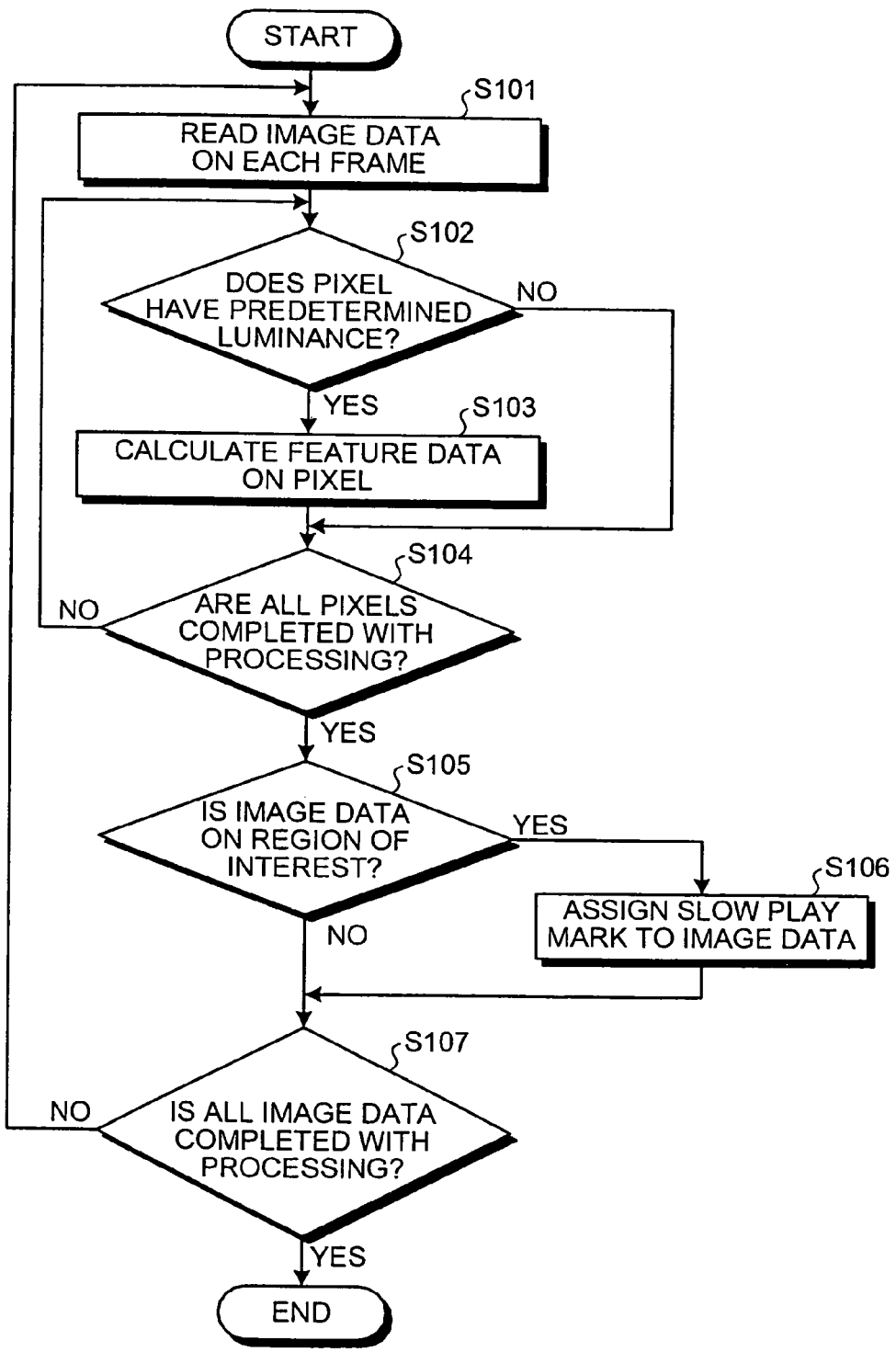
FIG. 3 is a flowchart for explaining processing procedures for extracting image data on a region of interest from a series of image data.

A processing performed by the image extracting unit 15a for extracting image data on the region of interest from the series of image data as image data the image corresponding to which is to be displayed on the display unit 12 at slow display frame rate will next be described. FIG. 3 is a flowchart for explaining processing procedures for extracting the image data on the region of interest from the series of image data loaded from the portable recording medium 5. Referring to FIG. 3, the control unit 15 reads the series of image data stored in the portable recording medium 5 in the reader-writer 13 frame by frame based on instruction information input from the input unit 11 (step S101).

If the control unit 15 reads the one-frame image data at the step S101, the image extracting unit 15a detects a luminance of one pixel that constitutes the one-frame image data, and determines whether the pixel is a pixel having a predetermined luminance based on the detected luminance (step S102). If determining that the pixel is a pixel having a predetermined luminance (step S102, Yes), the image extracting unit 15a calculates feature data on the pixel having the predetermined luminance (step S103). The image extracting unit 15a can thereby obtain color information on the pixel having the predetermined luminance. Thereafter, the control unit 15 determines whether all pixels that constitute the one-frame image data read at the step S101 are completed with the processing at the step S102 or S103 (step S104). On the other hand, if determining that the pixel is not a pixel having a predetermined luminance (step S102, No), the image extracting unit 15a does not perform the processing for calculating feature data on the pixel that does not have the predetermined luminance, and the control unit 15 performs a processing at and after the step S104.

Thereafter, if the control unit 15 determines that all the pixels included in the one-frame image data are not completed with the processing (step S104, No), the image extracting unit 15a repeats the processing at and after the step S102. Namely, the image extracting unit 15a can acquire feature data on all the pixels each having the predetermined luminance among all the pixels included in the one-frame image data by repeating the processing at the steps S102 to S104.

If acquiring the feature data on all the pixels each having the predetermined luminance, the image extracting unit 15a determines that all the pixels included in the one-frame image data are completed with the processing (step S104, Yes). In this case, the image extracting unit 15a determines whether the one-frame image data is image data on the region of interest, that is, image data on the bleeding site based on the acquired feature data on all the pixels (step S105). As described, the image extracting unit 15a detects whether read elements are present and distributed in the image data using the acquired feature data on all the pixels, and can determine whether the image data is the image data on the bleeding site based on the detection result at the step S105. Specifically, if the number of pixels each including a red element is equal to or greater than a predetermined threshold among all the pixels that constitute the one-frame image data, the image extracting unit 15a determines that the one-frame image data is the image data on the bleeding site.

If determining that the one-frame image data is image data on the region of interest at the step S105 (step S105, Yes), then the image extracting unit 15a can extract the one-frame image data as the image data on the region of interest, that is, the image data on the bleeding site, and assigns a slow play mark to the extracted image data (step S106). The control unit 15 stores the image data, to which the slow play mark is assigned, in the storage unit 14. It is to be noted that the slow play mark is a flag assigned to image data an image corresponding to which is displayed at slow display frame rate. Thereafter, the control unit 15 determines whether all of the series of image data stored in the portable recording medium 5 is completed with the processing at the steps S101 to S106 (step S107). On the other hand, if determining that the one-frame image data is not the image data on the region of interest at the step S105 (step S105, No), the image extracting unit 15a does not assign the slow play mark to the image data that is not the image data on the region of interest (bleeding site). In this case, the control unit 15 stores the image data, to which no slow play mark is assigned, in the storage unit 14, and performs processing at and after the step S107.

Thereafter, if determining at the step S107 that all the series of image data stored in the portable recording medium 5 are not completed with the processing at the steps S101 to S106 (step S107, No), the control unit 15 repeats the processing at and after the step S101. Namely, by causing the control unit 15 to repeat the processing at the steps S101 to S107, the image extracting unit 15a can determine whether each of the series of image data stored in the portable recording medium 5 is the image data on the bleeding site, and assign the slow play mark to each of all the image data on the bleeding site among the series of image data.

If determining at the step S107 that all the series of image data are completed with the processing at the steps S101 to S106 (step S107, Yes), the control unit 15 finishes the processing for reading the series of image data. In this case, the storage unit 14 stores therein the series of image data in which the slow play mark is assigned to each of all the image data on the bleeding site.

Figure 4:
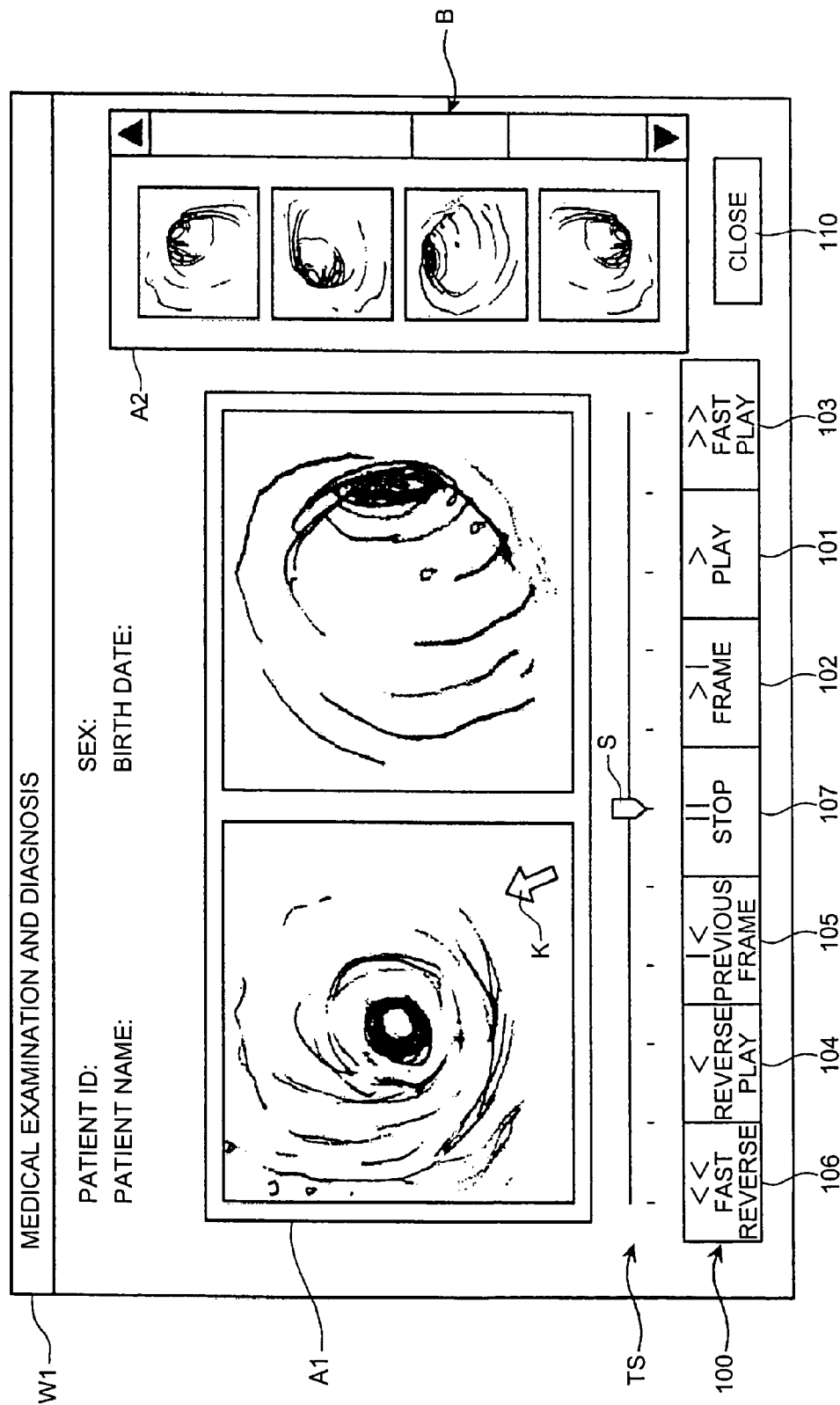
FIG. 4 is a pattern diagram specifically showing an example of a display screen of a display unit.

Next, an operation performed by the control unit 15 for causing the display unit 12 to display the images of the subject 1 will be described in detail while specifically showing an example of a display screen of the display unit 12. FIG. 4 is a pattern diagram specifically showing an example of the display screen of the display unit 12.

As shown in FIG. 4, a main-image display area A1 for displaying the images of the subject 1 picked up by the capsule endoscope 2, and a subimage display area A2 for displaying thumbnails corresponding to desired images selected from among those shown in the main-image display area A1 are formed in a window W1. Furthermore, a play-operation icon group 100 for performing various play operations for the images displayed in the main-image display area, a timescale TS for indicating time passing since start of picking up the series of images by the capsule endoscope 2, and a slider S pointing out the passing time since start of picking up an image displayed in the main-image display area A1 among that indicated by the timescale TS are formed in the window W1. Moreover, a scrollbar B for scrolling each thumbnail displayed in the subimage display area A2 is displayed near the subimage display area A2. Furthermore, the patient information such as the patient ID, the sex, the name, and the birth date of the subject 1, and a CLOSE icon 110 for performing an operation for closing the window W1 are displayed in the window W1.

The examiner performs an operation for putting a cursor K on and clicking on one of icons in the play-operation icon group 100 using the input unit 11 to display images of the subject 1 in the main-image display area A1. The input unit 11 inputs image-display instruction information corresponding to the icon selected by the click operation from among those in the play-operation icon group 100, to the control unit 15. If the control unit 15 detects the image-display instruction information from the input unit 11, the frame rate controller 15b decides that a display frame rate for the images to be displayed in the main-image display area A1 is a display frame rate corresponding to the image-display instruction information. The control unit 15 sequentially displays a series of images of the subject 1 in the main-image display area A1 at the display frame rate decided by the frame rate controller 15b.

If the examiner performs a click operation for selecting, for example, a PLAY icon 101 in the play-operation icon group 100, the input unit 11 inputs image-display instruction information (forward-play instruction information) corresponding to the PLAY icon 101 to the control unit 15. In this case, the frame rate controller 15b decides that the display frame rate for the series of images is a standard display frame rate along a forward direction of the time series based on the forward-play instruction information. Likewise, if the examiner performs a click operation for selecting a FRAME icon 102 in the play-operation icon group 100, then image-display instruction information (forward-frame-play instruction information) corresponding to the FRAME icon 102 is input to the control unit 15, and the frame rate controller 15b decides that the display frame rate for the series of images is slow display frame rate along the forward direction of the time series based on the forward-frame-play instruction information. Furthermore, if the examiner performs a click operation for selecting a FAST PLAY icon 103 in the play-operation icon group 100, then image-display instruction information (forward-fast-play instruction information) corresponding to the FAST PLAY icon 103 is input to the control unit 15, and the frame rate controller 15b decides that the display frame rate for the series of images is fast display frame rate along the forward direction of the time series based on the forward-fast-play instruction information.

Moreover, if the examiner performs a click operation for selecting a REVERSE PLAY icon 104 in the play-operation icon group 100, then image-display instruction information (reverse-play instruction information) corresponding to the REVERSE PLAY icon 104 is input to the control unit 15. In this case, the frame rate controller 15b decides that the display frame rate for the series of images is standard display frame rate along an opposite direction to the time series based on the reverse-play instruction information. Likewise, if the examiner performs a click operation for selecting a PREVIOUS FRAME icon 105 in the play-operation icon group 100, then image-display instruction information (previous-frame-play instruction information) corresponding to the PREVIOUS FRAME icon 105 is input to the control unit 15, and the frame rate controller 15b decides that the display frame rate for the series of images is slow display frame rate along the opposite direction to the time series based on the previous-frame-play instruction information. If the examiner performs a click operation for selecting a FAST REVERSE icon 106 in the play-operation icon group 100, then image-display information (reverse-and-fast play instruction information) corresponding to FAST REVERSE icon 106, and the frame rate controller 15b decides that the display frame rate for the series of images is fast display frame rate along the opposite direction to the time series based on the fast-reverse play instruction information.

It is to be noted that the standard display frame rate is a display frame rate to the extent that a series of images can be pseudo-played as a moving image. Further, the slow display frame rate is slower than the standard display frame rate, and time for displaying each image at the slow display frame rate is set longer than time for displaying each image at the standard frame rate. The slow display frame rate is, for example, a display frame rate to the extent that a series of images can be easily observed frame by frame. Moreover, the fast display frame rate is faster than the standard display frame rate, and time for displaying each image at the fast display frame rate is set shorter than the time for displaying each image at the standard frame rate.

The control unit 15 controls the display unit 12 to sequentially displays the series of images at the display frame rate decided by the frame rate controller 15b, irrespectively of to which rate the display frame rate is set. In this case, if the number of images displayed at once in the main-image display area A1 is set in advance, the control unit 15 controls the display unit 12 to display the desired number of images thus set in the main-image display area A1.

If the examiner performs a click operation for selecting a STOP icon 107 in the play-operation icon group 100, the input unit 11 inputs image-display instruction information (stop instruction information) corresponding to the STOP icon 107 to the control unit 15. In this case, the control unit 15 temporarily stops a switching processing on the images displayed in the main-image display area A1, and maintains the images displayed in the main-image display area A1 at the time of performing the click operation for selecting the STOP icon 107 as still images.

If the examiner performs a click operation for selecting an image displayed in the main-image display area A1, the control unit 15 controls the display unit 12 to display a thumbnail corresponding to the image selected and instructed by the click operation in the subimage display area A2. In this case, the control unit 15 controls the display unit 12 to sequentially add the thumbnail corresponding to the selected image to those in the subimage display area A2 whenever this image-selecting click operation is performed.

Figure 5:
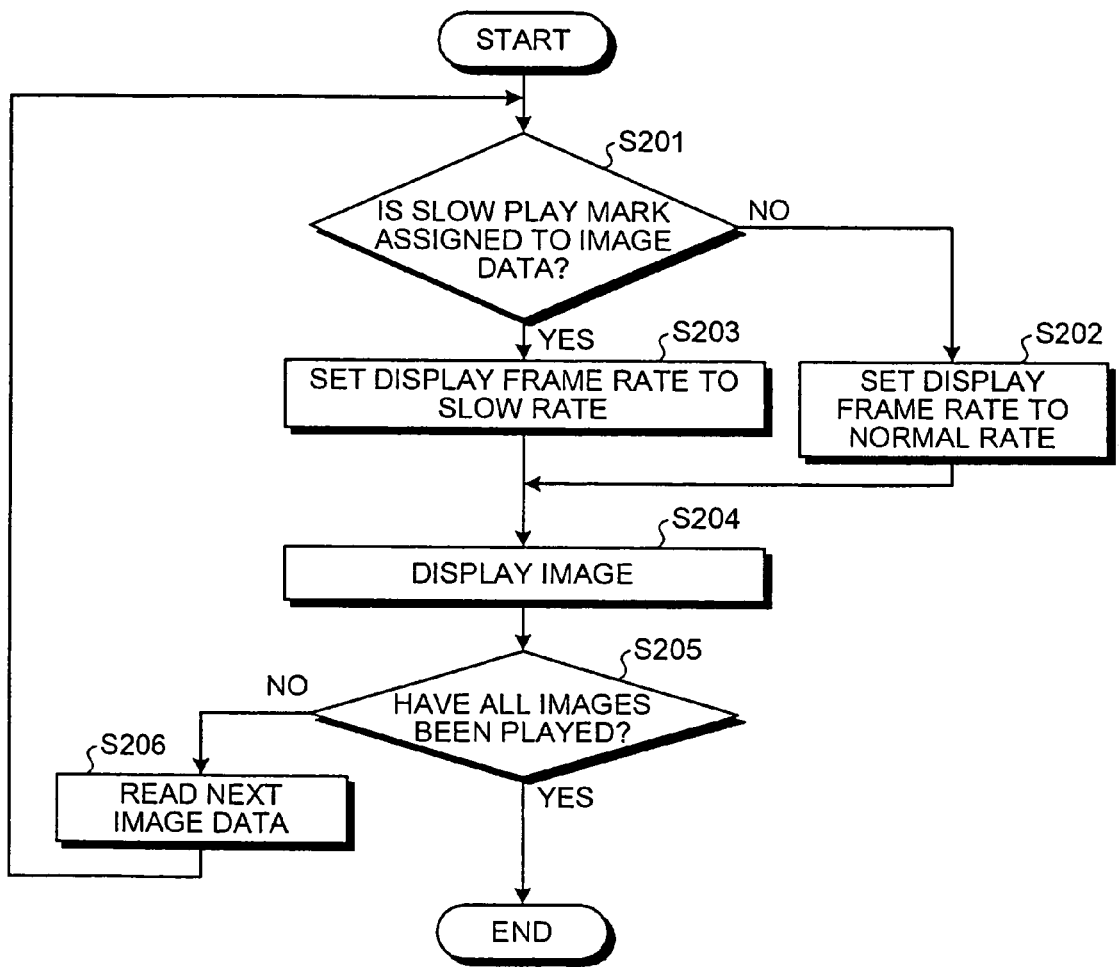
FIG. 5 is a flowchart for explaining processing procedures for sequentially displaying images corresponding to a series of image data including image data to which a slow play mark is assigned.
Figure 6:
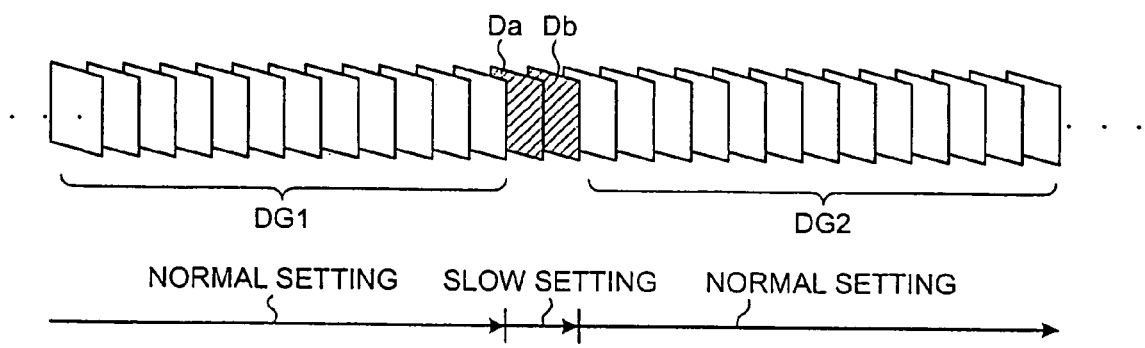
FIG. 6 is a pattern diagram for explaining an operation for setting a display frame rate for each of a series of image data including the automatically-extracted image data on the region of interest.

An operation performed by the control unit 15 for sequentially displaying a series of images of the subject 1 based on the series of image data including the image data to each of which the slow play mark is assigned will next be described. FIG. 5 is a flowchart for explaining processing procedures for sequentially displaying images corresponding to the series of image data including the image data to each of which the slow play mark is assigned. FIG. 6 is a pattern diagram for explaining an operation for setting a display frame rate for each of the series of image data including the automatically extracted image data on the region of interest. First, the examiner performs an operation for selecting a series of image data the images corresponding to which are to be displayed in the main-image display area A1 using the input unit 11, and performs a click operation for selecting one of the icons in the play-operation icon group 100. In this case, the control unit 15 receives the image-display instruction information corresponding to one of the icons in the play-operation icon group 100 as already stated. In FIG. 5, the control unit 15 reads the image data the images corresponding to which are to be displayed in the main-image display area A1 among the series of image data on the subject 1 stored in the storage unit 14, with reception of this image-display instruction information from the input unit 11 as a trigger. In this case, the control unit 15 determines whether the slow play mark is assigned to image data read from the storage unit 14 (step S201).

If the control unit 15 cannot detect the slow play mark from the read image data, the control unit 15 determines that the image data is image data to which no slow play mark is assigned (step S201, No). In this case, the frame rate controller 15b sets the display frame rate for this image data to normal rate (step S202). Namely, the frame rate controller 15b decides that the display frame rate for the image data from which no slow play mark is detected is the normal display frame rate corresponding to the image-display instruction information input from the input unit 11.

If the control unit 15 detects the slow play mark from the read image data, the control unit 15 determines that the image data is image data to which the slow play mark is assigned (step S201, Yes). In this case, the frame rate controller 15b changes the display frame rate for this image data from the normal rate to slow rate based on the detected slow play mark (step S203). Namely, the frame rate controller 15b decides that the display frame rate for the image data to which the slow play mark is assigned is the slow display frame rate.

As shown in FIG. 6, for example, the frame rate controller 15b sets a display frame rate for each image data in an image data group DG1, to each of which no slow play mark is assigned, among the series of image data to the normal rate, changes a display frame rate for each of image data Da and Db (e.g., image data on the bleeding site), to each of which the slow play mark is assigned, to the slow rate, and sets a display frame rate for each image data in an image data group DG2, to each of which no slow play mark is assigned, to the normal rate.

If the frame rate controller 15b decides the display frame rate for each image data, the control unit 15 controls the display unit 12 to display an image of the subject 1 corresponding to each image data at the display frame rate decided by the frame rate controller 15b (step S204). Namely, if an image corresponding to the image data to which no slow play mark is assigned (e.g., each image data in the image data groups DG1 and DG2) is to be displayed in the main-image display area A1, the control unit 15 controls the display unit 12 to display the image at the normal display frame rate corresponding to one of the icons in the play-operation icon group 100. If an image corresponding to the image data to which the slow play mark is assigned (e.g., each of image data Da and Db) is to be displayed in the main-image display area A1, the control unit 15 controls the display unit 12 to display the image forcedly at the slow display frame rate, irrespectively of the image-display instruction information input from the input unit 11. That is, even if the PLAY icon 101 or the FAST PLAY icon 103 is selected by the click operation performed by the examiner, the control unit 15 controls the display unit 12 to display the image corresponding to the image data, to which the slow play mark is assigned, forcedly at the slow display frame rate. The image corresponding to the image data to which the slow play mark is assigned (that is, the image data on the region of interest) is thereby displayed for longer time than those corresponding to the other image data, thus facilitating examiner's observation.

Thereafter, the control unit 15 determines whether all images corresponding to the series of image data the images corresponding to which are designated to be displayed by the examiner have been played in the main-image display area A1 (step S205). If determining that all the images designated to be displayed have not been played yet (step S205, No), then the control unit 15 reads next image data temporally continuous to the image data, the image corresponding to which is displayed at the step S204, from the storage unit 14 (step S206), and repeats the processing at and after the step S201 using the read image data. Namely, the control unit 15 sequentially performs the processing at and after the step S201 on each of all the series of image data the images corresponding to which are designated to be displayed. If determining that all the images designated to be displayed have been played yet (step S205, Yes), the control unit 15 finishes the processing for displaying the images corresponding to the series of image data the images corresponding to which are designated to be displayed.

In the first embodiment of the present invention, when a series of image data stored in the portable recording medium 5 is to be loaded, the slow play mark is assigned to each image data on the region of interest among the series of image data. However, the present invention is not limited thereto. A processing for assigning the slow play mark to each of the image data among the series of image data stored in the storage unit 14 can be performed as long as the image data is that on the region of interest. Alternatively, a processing for assigning the slow play mark to each of the series of image data almost at real time can be performed when the images corresponding to the series of image data are sequentially displayed. Namely, when the images corresponding to the series of image data stored in the storage unit 14 are sequentially displayed, a processing for successively reading image data on a desired number of frames, e.g., about five frames prior to display of the images, and for assigning the slow play mark to each of the image data on the desired frames thus read can be performed as long as the image data is that on the region of interest.

Furthermore, in the first embodiment of the present invention, the bleeding site has been explained as an example of the region of interest in which the examiner is interested, and the images corresponding to the image data on the bleeding site are displayed among the series of image data. However, the present invention is not limited thereto. A lesion site such as a tumor or a desired observation-target organ can be set as the region of interest, and images corresponding to image data on the lesion site or the desired observation-target region can be displayed at the slow display frame rate among the series of image data. In this case, the image data on the lesion site or the desired observation-target region can be extracted from the series of image data based on feature data on each pixel included in the image data.

Moreover, in the first embodiment of the present invention, the image corresponding to the image data, to which the slow play mark is assigned, is displayed at the same display frame rate as the normally-set slow display frame rate to correspond to the FRAME icon 102 or the PREVIOUS FRAME icon 105. However, the present invention is not limited thereto. An image corresponding to the image data, to which the slow play mark is assigned, can be displayed always at slower display frame rate than the normally-set display frame rate, that is, the display frame rate set by the play-operation icon group 100. In this case, a display frame rate slower than the normally-set display frame rate by a certain rate, e.g., set to be ½ of the normally-set display frame rate. Multiple rates changed according to the fast, standard, and slow display frame rates, respectively can be set, and it can be decided that the display frame rate for the image data to which the slow play mark is assigned is the display frame rate slower than the normally-set display frame rate by the multiple rates, e.g., set to be ¼ thereof for the fast display frame rate, ⅓ thereof for the standard display frame rate, and ½ thereof for the slow display frame rate.

Furthermore, in the first embodiment of the present invention, only the images of the region of interest such as the bleeding site are displayed at the slower display frame rate than the display frame rate for displaying the images of the other regions. However, the present invention is not limited thereto. The display frame rate for at least one of temporally previous and next images to the image of the region of interest can be changed to the same display frame rate as that for displaying the image of the region of interest, and not only the images of the region of interest but also at least one of the temporally previous and next images can be displayed at the slow rate. In this case, it suffices that the image extracting unit 15a assigns the slow play mark to at least one of temporally previous and next image date to the extracted image data on the region of interest.

Moreover, in the first embodiment of the present invention, the images of the region of interest are displayed at the slower display frame rate than the display frame rate for the images of the regions other than the region of interest by setting the display frame rate for the images of the region of interest such as the bleeding site slower than the normal display frame rate. However, the present invention is not limited thereto. The display frame rate for the region of interest can be set relatively slower than the display frame rate for the regions other than the region of interest by setting the display frame rate for the images of the regions other than the region of interest faster than the normal display frame rate.

As described so far, in the first embodiment of the present invention, the image display apparatus is configured to automatically change the display frame rate for the image data obtained by imaging the region of interest such as the bleeding site among the series of image data the images corresponding to which are to be displayed, to the slower rate than the normally-set display frame rate, and to display the images corresponding to the image data on the region of interest forcedly at the slower rate if the series of image data are to be sequentially displayed. It is thereby possible to realize the image display apparatus that can automatically display the images corresponding to the image data on the region of interest at the slow rate even if the display frame rate normally set when images corresponding to the series of image data are to be sequentially displayed is set to the fast or standard rate, and that can shorten the time for observing the series of images of the subject without hampering observation of the images of the region of interest.

The examiner can automatically display the images of the region of interest and images similar thereto, i.e., to-be-observed images at the slow rate by employing the image display apparatus according to the present invention. It is thereby possible for the examiner to observe (examine) the subject while narrowing down the images to the to-be-observed images displayed at the slow rate, to efficiently observe the series of images, to easily observe the images of the region of interest, and to accurately diagnose the subject.

Second Embodiment

A second embodiment of the present invention will be described. In the first embodiment, the images of the preset, certain region of interest are displayed at the slow rate among the series of images of the subject. In the second embodiment, a desired region of interest can be selected from among options of regions in the body of the subject.

Figure 7:
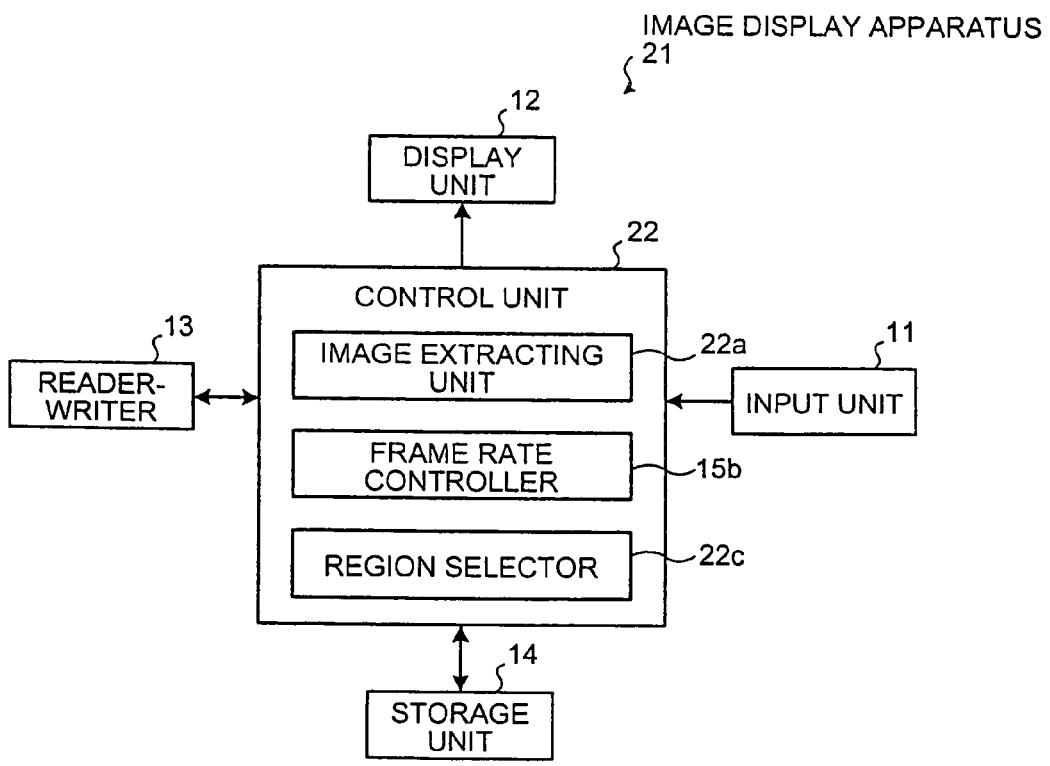
FIG. 7 is a block diagram typically showing an example of a configuration of an image display apparatus according to a second embodiment of the present invention.

FIG. 7 is a block diagram typically showing an example of a configuration of an image display apparatus according to the second embodiment of the present invention. An image display apparatus 21 includes a control unit 22 in place of the control unit 15 of the image display apparatus 4 according to the first embodiment. The control unit 22 includes an image extracting unit 22a in place of the image extracting unit 15a according to the first embodiment. The other constituent elements are identical to those according to the first embodiment, and the same constituent elements are denoted by the same reference symbols, respectively.

The control unit 22, which functions almost similarly to the control unit 15, includes the image extracting unit 22a, the frame rate controller 15b, and a region selector 22c. The image extracting unit 22a extracts image data on a region of interest alternatively decided by the region selector 22c among a series of image data on the subject 1, and assigns a slow play mark to the extracted image data. In this case, the image extracting unit 22a identifies an imaged region of the image data based on feature data on each of pixels that constitute the image data. For example, the image extracting unit 22a determines whether the imaged region of the image data is a bleeding site based on whether red elements are present and distributed in the image data, and identifies the imaged region as the bleeding site based on the determination result. Furthermore, the image extracting unit 22a determines which organ, e.g., the esophagus, the stomach, the small intestine or the large intestine is the imaged region of the image data based on statistic values related to color information such as an average color of the image data and the number of pixels of a predetermined color included in one frame, and identifies this imaged region as the organ based on the determination result.

Figure 8:
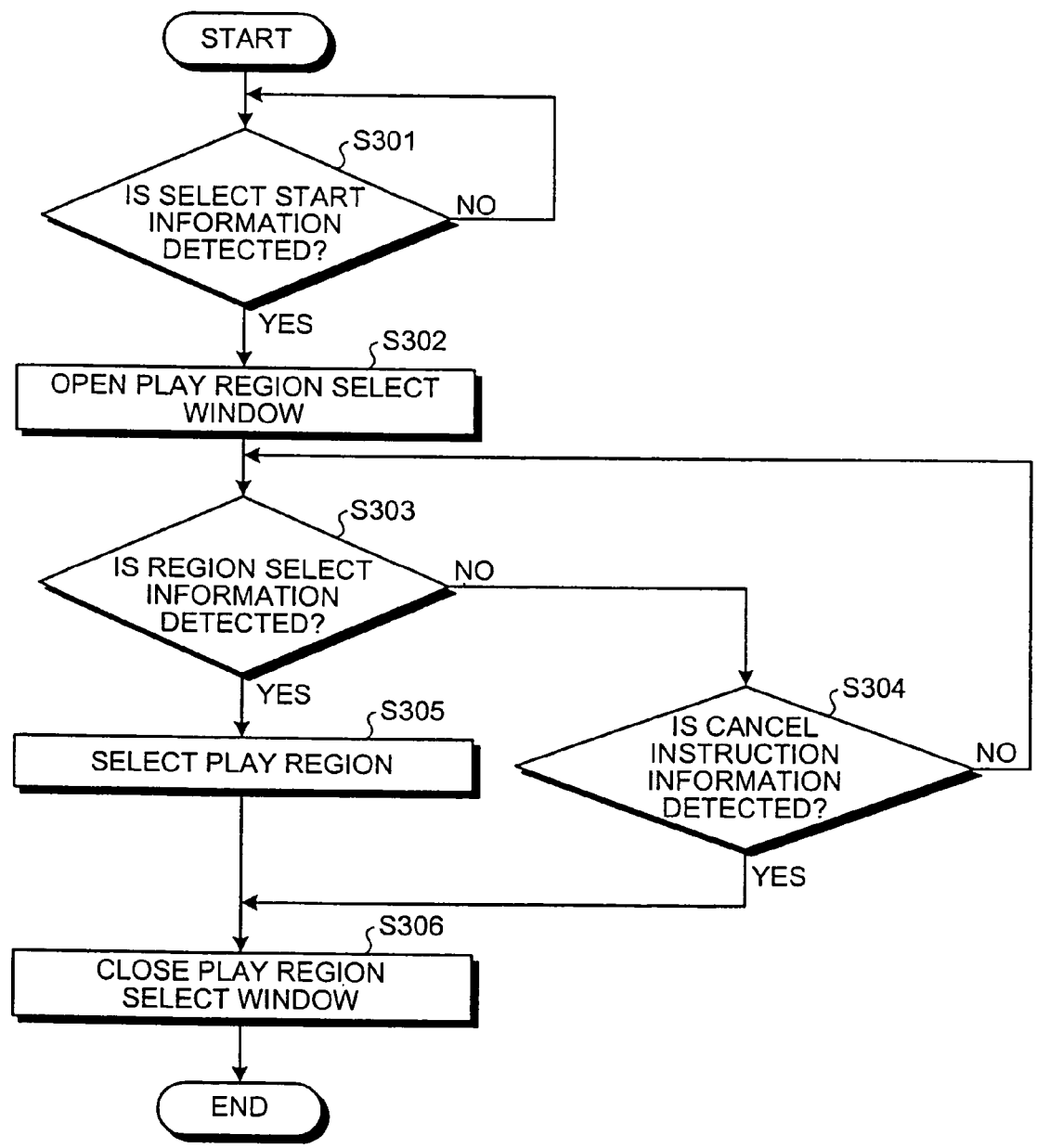
FIG. 8 is a flowchart for explaining processing procedures for selecting a play region.
Figure 9:
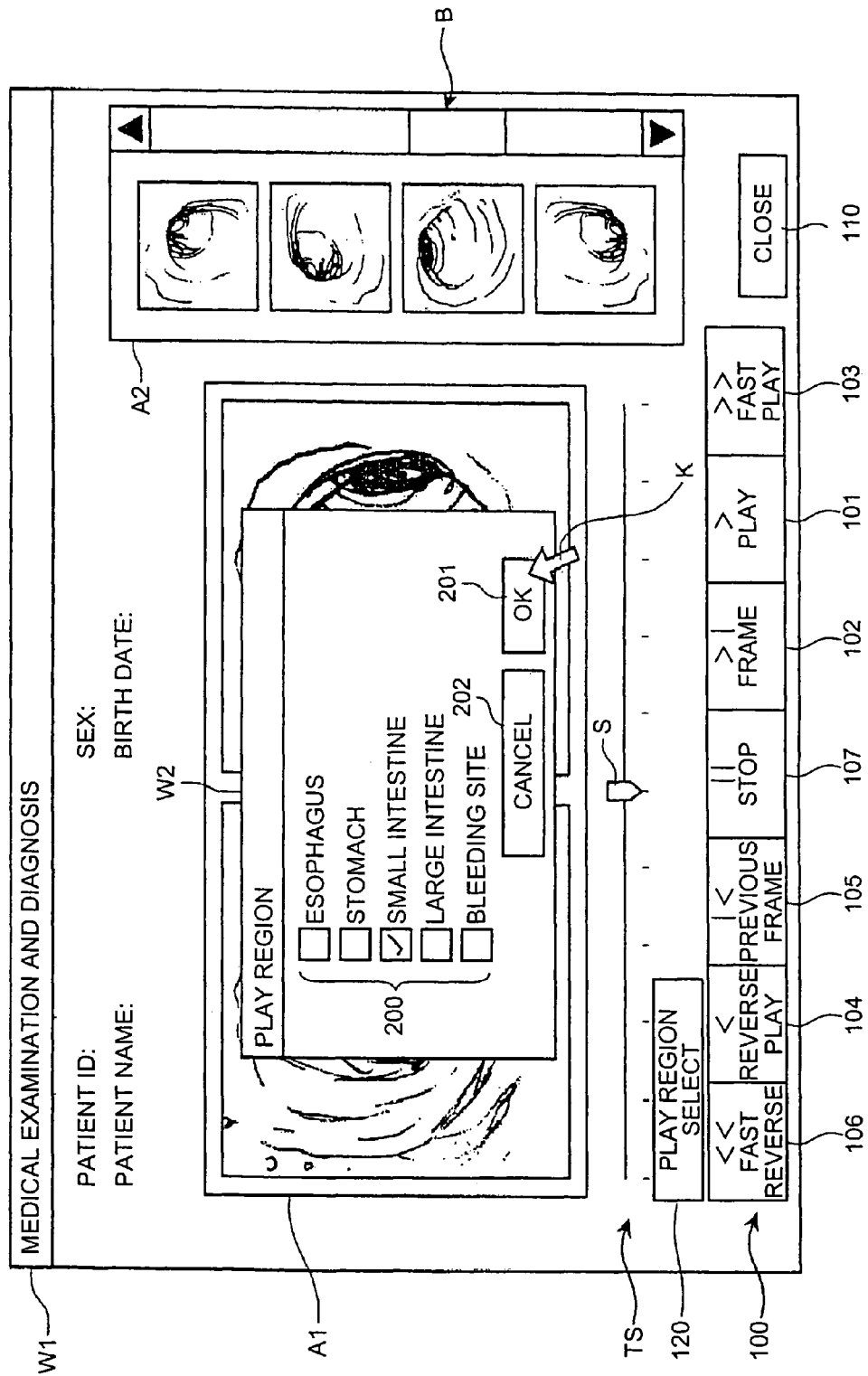
FIG. 9 is a pattern diagram specifically showing a display screen for selecting the play region.

Moreover, the region selector 22c selects the region alternatively designated by the examiner using the input unit 11 as the region of interest (play region) the images of which are to be displayed among preset options of regions of the subject. FIG. 8 is a flowchart for explaining processing procedures for selecting the play region from among the regions of the subject. FIG. 9 is a pattern diagram specifically showing an example of a display screen for selecting the play region from among the options of regions of the subject.

Referring to FIGS. 8 and 9, the control unit 22 controls the display unit 12 to further display a PLAY REGION SELECT icon 120 in a predetermined display area in the window W1. If the examiner performs a click operation for putting the cursor K and clicking on the PLAY REGION SELECT icon, that is, for selecting the PLAY REGION SELECT icon 120 using the input unit 11, the input unit 11 inputs instruction information (select start information) for instructing start of a play-region selection processing to the control unit 22. The control unit 22 constantly monitors the select start information, and if the select start information is input to the control unit 22, then the control unit 22 detects the select start information (step S301, Yes), and controls the display unit 12 to open a play-region select window W2 (step S302). It is to be noted that the control unit 22 repeats the processing at the step S301 and monitors the select start information if not detecting the select start information (step S301, No).

As shown in FIG. 9, options 200 of the regions of the subject, an OK icon 201, and a CANCEL icon 202 are displayed in the select window W2. The examiner performs an input operation for selecting the play region from among the options 200 using the input unit 11, whereby the examiner can input the region selection information corresponding to the selected play region to the control unit 22. For example, by putting the cursor K and clicking on the "small intestine" in the options 200 and then putting the cursor K and clicking on the OK icon 201, the examiner can input the region selection information corresponding to the "small intestine" alternatively designated as the play region to the control unit 22.

If the control unit 22 causes the display unit 12 to display the select window W2, the control unit 22 monitors the region selection information. If the region selection information is input to the control unit 22 from the input unit 11, the control unit 22 detects the region selection information (step S303, Yes). In this case, the region selector 22 selects, as the play region, the region corresponding to the region selection information detected at the step S303 from among the options of the regions of the subject, e.g., the esophagus, the stomach, the small intestine, and the large intestine (step S305), and stores the selected play region. Thereafter, the control unit 22 controls the display unit 12 to close the select window W2 (step S306), thus completing the play-region selection processing.

On the other hand, if the examiner is to close the select window W2 without selecting the play region, the examiner performs an input operation for selecting the CANCEL icon 202. By this input operation, instruction information (cancel instruction information) for closing the select window W2 without selecting the play region is input to the control unit 22. In this case, the control unit 22 does not detect the region selection information at the step S303 (step S303, No), and detects the cancel instruction information input from the input unit 11 (step S304, Yes). Thereafter, the control unit 22 performs the processing at a step S306 without performing the processing at a step S305. If the cancel instruction information is not input to the control unit 22 in a state in which the select window W2 is open on the screen, then the control unit 22 does not detect the cancel instruction information (step S304, No), and repeats the processing at and after the step S303.

Figure 10:
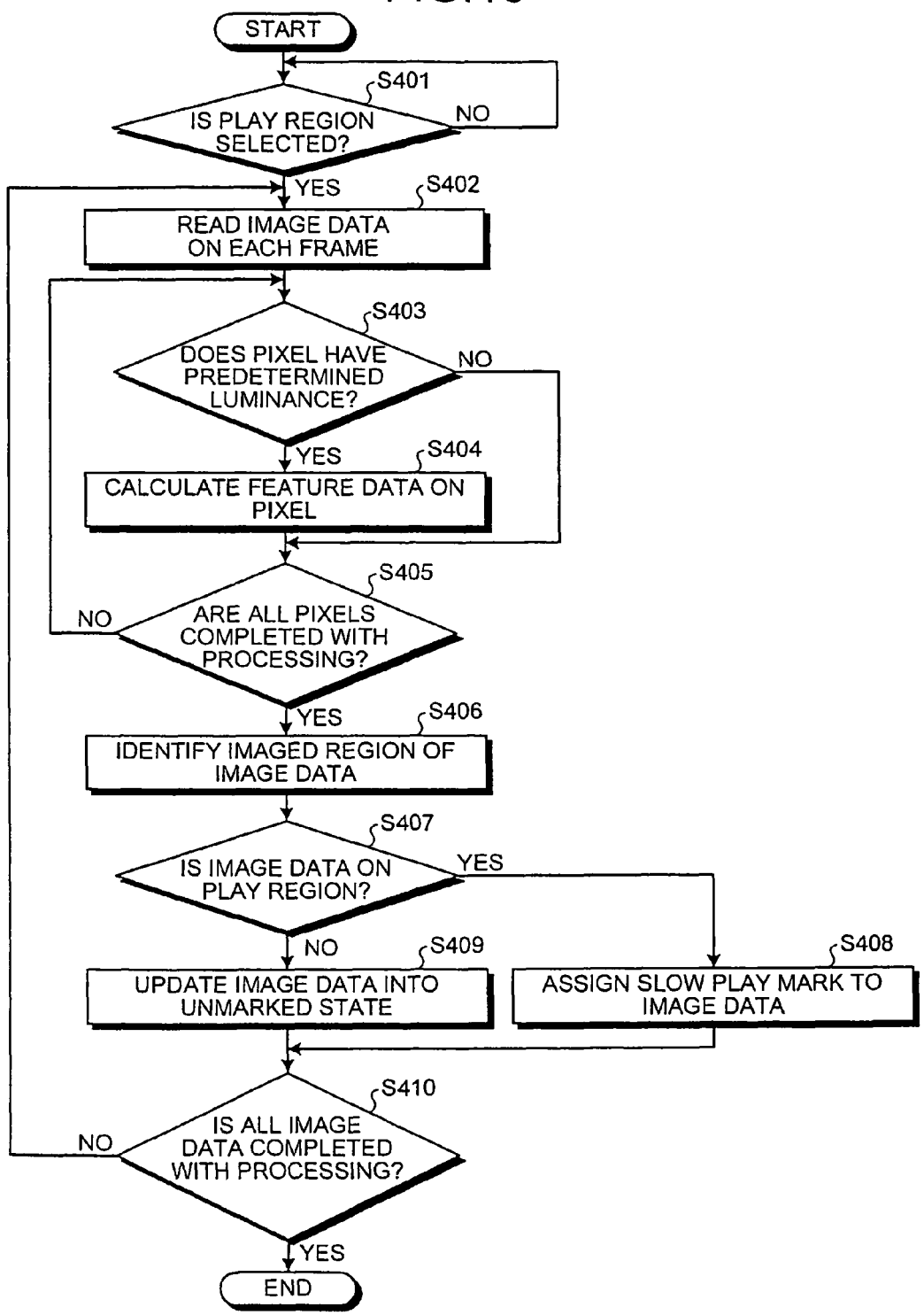
FIG. 10 is a flowchart for explaining processing procedures for assigning a slow play mark to image data on the selected play region.

A processing for assigning the slow play mark to the image data on the play region selected by the region selector 22c from among a series of image data on the subject 1 will next be described. FIG. 10 is a flowchart for explaining processing procedures for assigning the slow play mark to the image data on the play region selected by the region selector 22c. In FIG. 10, the control unit 22 determines whether the play region is selected by the region selector 22c (step S401). If determining that the play region is not selected (step S401, No), the control unit 22 repeats the step S401. If determining that the play region is selected (step S401, Yes), then the control unit 22 perform the same processing as that at the steps S101 to S104 using the series of image data on the subject 1 stored in the portable recording medium 5 or the storage unit 14, and acquires feature data on the respective pixels that constitute the read one-frame image data (steps S402 to S405).

If acquiring the feature data on the respective pixels, the image extracting unit 22a identifies the imaged region of the one-frame image data based on the acquired feature data (step S406). The image extracting unit 22a identifies the image region as, for example, one of the esophagus, the stomach, the small intestine, the large intestine, and the bleeding site in the options 200 by performing the processing at the step S406.

Next, the image extracting unit 22a determines whether the imaged region of the image data identified at the step S406 coincides with the play region selected by the region selector 22c (step S407). If determining that the imaged region of the image data coincides with the selected play region, then the image extracting unit 22a determines that the image data on the identified imaged region is image data on the play region and extracts the image data (step S407, Yes), and assigns the slow play mark to the extracted image data on the imaged region (step S408). The control unit 22 stores the image data, to which the slow play mark is assigned, in the storage unit 14.

If determining that the imaged region of the image data does not coincide with the selected play region, then the image extracting unit 22a determines that the image data on the identified imaged region is not image region on the play region (step S407, Yes). In this case, the image extracting unit 22a updates the image data different from that on the play region into a state in which no slow play mark is assigned to the image data (unmarked state) (step S409). Namely, the image extracting unit 22a does not assign the slow play mark to the image data different from that on the play region or erases the slow play mark assigned to the image data in advance.

Thereafter, the control unit 22 determines whether all of the series of image data on the subject 1 is completed with the processing at the steps S402 to S409 (step S410). If determining that all the image data on the subject 1 is not completed with the processing at the steps S402 to S409 (step S410, No), the control unit 22 repeats the processing at and after the step S402. Namely, by causing the control unit 22 to repeat the processing at and after the step S402, the image extracting unit 22a can identify the imaged region of each of the series of image data on the subject 1, and assign the slow play mark to each of all the image data on the play region among the series of image data.

If determining that all of the series of image data on the subject 1 is completed with the processing at the steps S402 to S409 at the step S410 (step S410, Yes), the control unit 22 completes the processing for reading the series of image data. In this case, the storage unit 14 stores therein the series of image data in which the slow play marks are assigned only to all the image data on the play region, respectively.

The control unit 22 reads the image data the images corresponding to which are to be displayed in the main-image display area A1 among the series of image data on the subject 1 stored in the storage unit 14, with the image-display instruction information input from the input unit 11 as a trigger, and performs the same processing as that at the steps S201 to S206. In this case, the frame rate controller 15*b* sets the display frame rate for the image data to which no slow play mark is assigned, i.e., the image data on a region other than the play region to normal rate, and changes the display frame rate for the image data to which the slow frame mark is assigned, i.e., the image data on the play region from the normal rate to slow rate.

Figure 11:
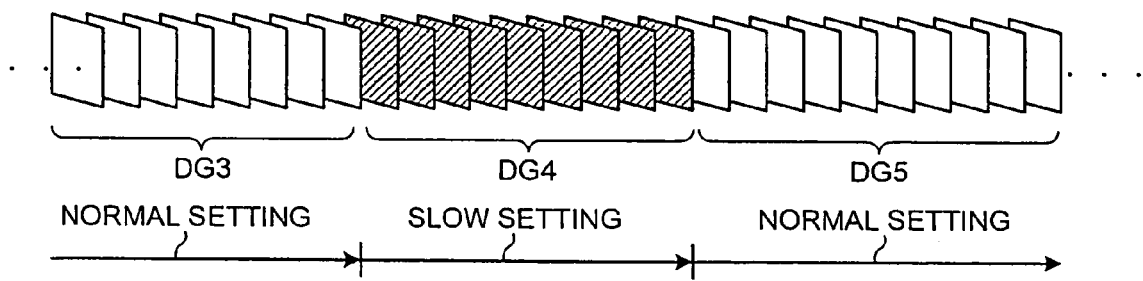
FIG. 11 is a pattern diagram for explaining a display frame rate for each of a series of image data including image data on the play region.

FIG. 11 is a pattern diagram for explaining an operation for setting the display frame rate for each of the series of image data including the image data on the play region. As shown in FIG. 11, for example, the frame rate controller 15*b* sets the display frame rate for each of image data, to each of which data no slow play mark is assigned, in an image data group DG3 on regions other than the play region among the series of image data on the subject 1 to normal rate, changes the display frame rate for each of image data, to each of which data the slow play mark is assigned, in an image data group DG4 on the play region to slow rate, and sets the display frame rate for each of image data, to each of which data no slow play mark is assigned, in an image data group DG5 on regions other than the play region to the normal rate.

The control unit 22 controls the display unit 12 to display the series of images of the subject 1 at the display frame rates decided by the frame rate controller 15*b*. Namely, if an image corresponding to the image data to which no slow play mark is assigned (e.g., each of the image data in the image data groups DG3 and DG5 on the regions other than the play region) is to be displayed in the main-image display area A1, the control unit 22 controls the display unit 12 to display the image at the normal display frame rate corresponding to one of the icons in the play-operation icon group 100. If an image corresponding to the image data to which the slow play mark is assigned (e.g., each of the image data in the image data group DG4 on the play region) is to be displayed in the main-image display area A1, the control unit 22 controls the display unit 12 to display the image forcedly at the slow display frame rate, irrespectively of the image-display instruction information input from the input unit 11. The image corresponding to the image data to which the slow play mark is assigned (that is, the image data on the play region) is thereby displayed for longer time than time for displaying the other image data, thus facilitating examiner's observation.

In the second embodiment of the present invention, the slow play mark is assigned only to each of the image data on the play region among the series of image data on the subject 1, with selection of the play region as a trigger. However, the present invention is not limited thereto. A processing for assigning the slow play mark to each of the series of image data almost at real time when each image is displayed can be performed. Namely, when images corresponding to the series of image data on the subject 1 are to be displayed sequentially, it is confirmed whether the play region is selected for the series of image data. If the play region is selected, then a processing for successively reading image data on a desired number of frames, e.g., about five frames prior to display of the images, and for assigning the slow play mark to each of the read image data on the desired frames can be performed.

Furthermore, in the second embodiment of the present invention, the stomach, the esophagus, the small intestine, the large intestine, and the bleeding site have been described as the options for selecting the play region by way of example. However, the present invention is not limited thereto. It suffices that desired regions of interest are set as the options, and not only the organs and the bleeding site of the subject but also, for example, a lesion site such as a tumor can be added as the options.

Moreover, in the second embodiment of the present invention, the play region that is the region of interest as the image display target is selected, and the images of the selected play region are displayed at the slow display frame rate. However, the present invention is not limited thereto. Regions of no interest for examination can be selected from among the options of the regions in the body of the subject, and images of the selected regions can be displayed at faster display frame rate than that for displaying the images of the region of interest.

Furthermore, in the second embodiment of the present invention, only the images of the selected play region are displayed at the slower display frame rate than that for displaying the other images. However, the present invention is not limited thereto. The display frame rate for at least one of temporally previous and next images to one of the images of the region of interest can be changed to the same display frame rate as that for displaying the images of the region of interest, and not only the images of the play region but also at least one of the temporally previous and next images can be displayed at the slow display frame rate. In this case, the image extracting unit 22*a* can assign the slow play mark to image data on at least one of the temporally previous and next images to the extracted image data on the play region.

As described so far, according to the second embodiment of the present invention, besides the functions and the configuration of the first embodiment, the image display apparatus is configured to be able to select the region of interest, the images of which are to be displayed at the slow rate, as the play region, and to display the images of the selected play region forcedly at slower rate if the image display apparatus is to sequentially display a series of images of the subject. It is, therefore, possible to realize the image display apparatus that can exhibit the functions and advantages of the first embodiment, that can easily switch the region of interest, the images of which are to be display at the slow rate, to the desired region of interest, and that can shorten the time for observing the series of images of the subject without hampering observation of the images of the selected, desired region of interest.

Third Embodiment

A third embodiment of the present invention will be described in detail. In the second embodiment, the images of the selected play region among the series of images of the subject are display at the slow rate, and the images other than those of the play region are displayed at normally-set display frame rate corresponding to one of the play-operation icon group 100. In the third embodiment, the display frame rate for images of regions other than the selected play region is changed to fast rate.

Figure 12:
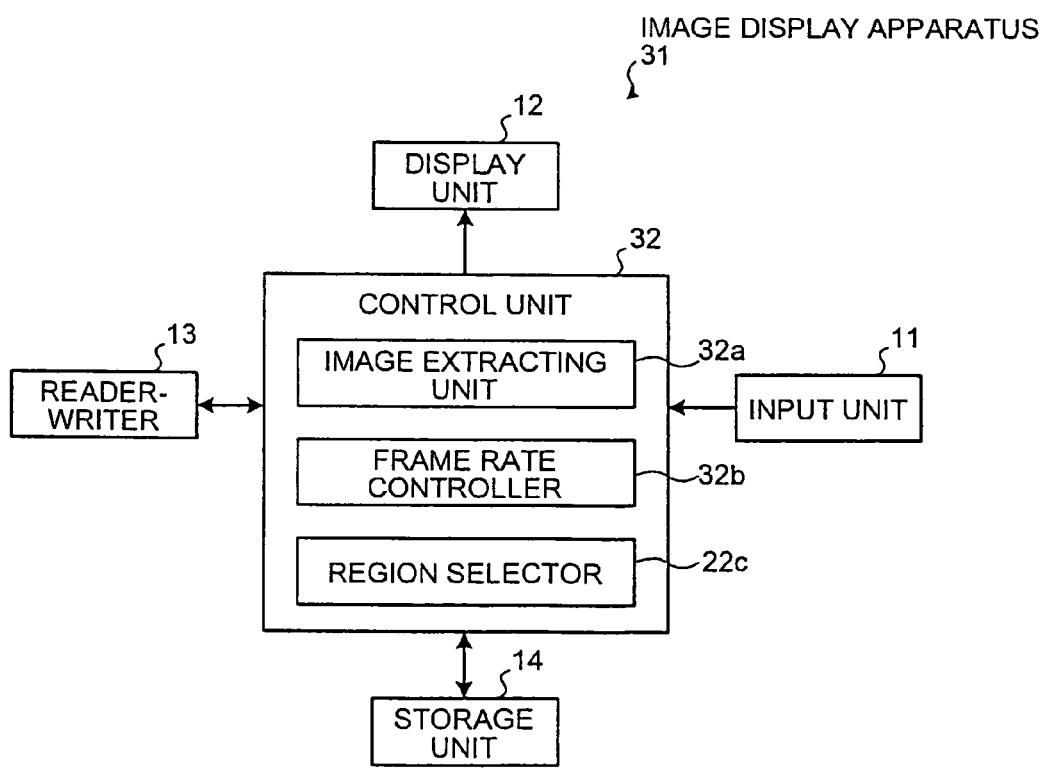
FIG. 12 is a block diagram typically showing an example of a configuration of an image display apparatus according to a third embodiment of the present invention.

FIG. 12 is a block diagram typically showing an example of a configuration of an image display apparatus according to the third embodiment of the present invention. An image display apparatus 31 includes a control unit 32 in place of the control unit 22 of the image display apparatus 21 according to the second embodiment. The control unit 32 includes an image extracting unit 32*a* in place of the image extracting unit 22a according to the second embodiment, and a frame rate controller 32b in place of the frame rate controller 15b. The other constituent elements are identical to those according to the second embodiment, and the same constituent elements are denoted by the same reference symbols, respectively.

The control unit 32, which functions almost similarly to the control unit 22, includes the image extracting unit 32a, the frame rate controller 32b, and the region selector 22c. The image extracting unit 32a, which functions almost similarly to the image extracting unit 22a, assigns a fast play mark to each of image data on regions other than the play region selected by the region selector 22c. The fast play mark is a flag assigned to image data, an image of which is to be displayed at fast display frame rate. Furthermore, the frame rate controller 32b functions almost similarly to the frame rate controller 15b, and further includes a function of changing the display frame rate for the image data, to which the fast play mark is assigned, to the fast display frame rate.

Figure 13:
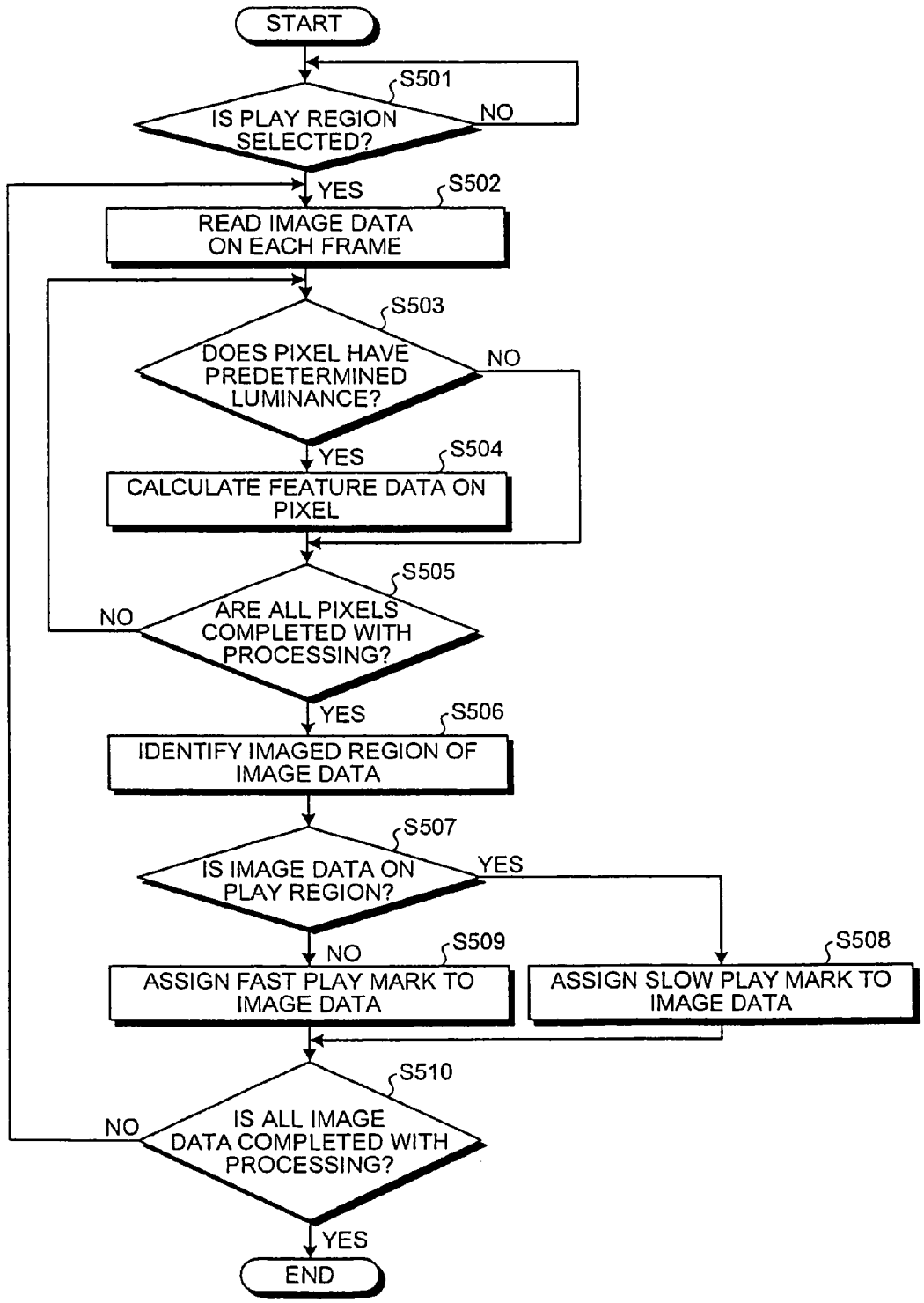
FIG. 13 is a flowchart for explaining processing procedures for assigning a slow play mark or a fast play mark to each of a series of image data for which the play region is selected.

FIG. 13 is a flowchart for explaining processing procedures for assigning the slow play mark or the fast play mark to each of a series of image data for which the play region is selected. If the play region is selected for a series of image data of the subject 1, the image extracting unit 32a assigns the slow play mark to each of all image data on the selected play region among the series of image data for which the play region is selected, and assigns the fast play mark to each of all the image data other than the image data on the play region. Namely, referring to FIG. 13, the control unit 32 performs a processing almost similarly to that at the steps S401 to S410 (steps S501 to S510), and acquires a series of image data on the subject 1 constituted by all the image data on the play region, to each of which data the slow play mark is assigned, and all the image data on the regions other than the play region, to each of which data the fast play mark is assigned. In this case, the image extracting unit 32a performs a processing for assigning the fast play mark to each of the image data on the regions other than the play region in place of the step S409 (step S509).

Figure 14:
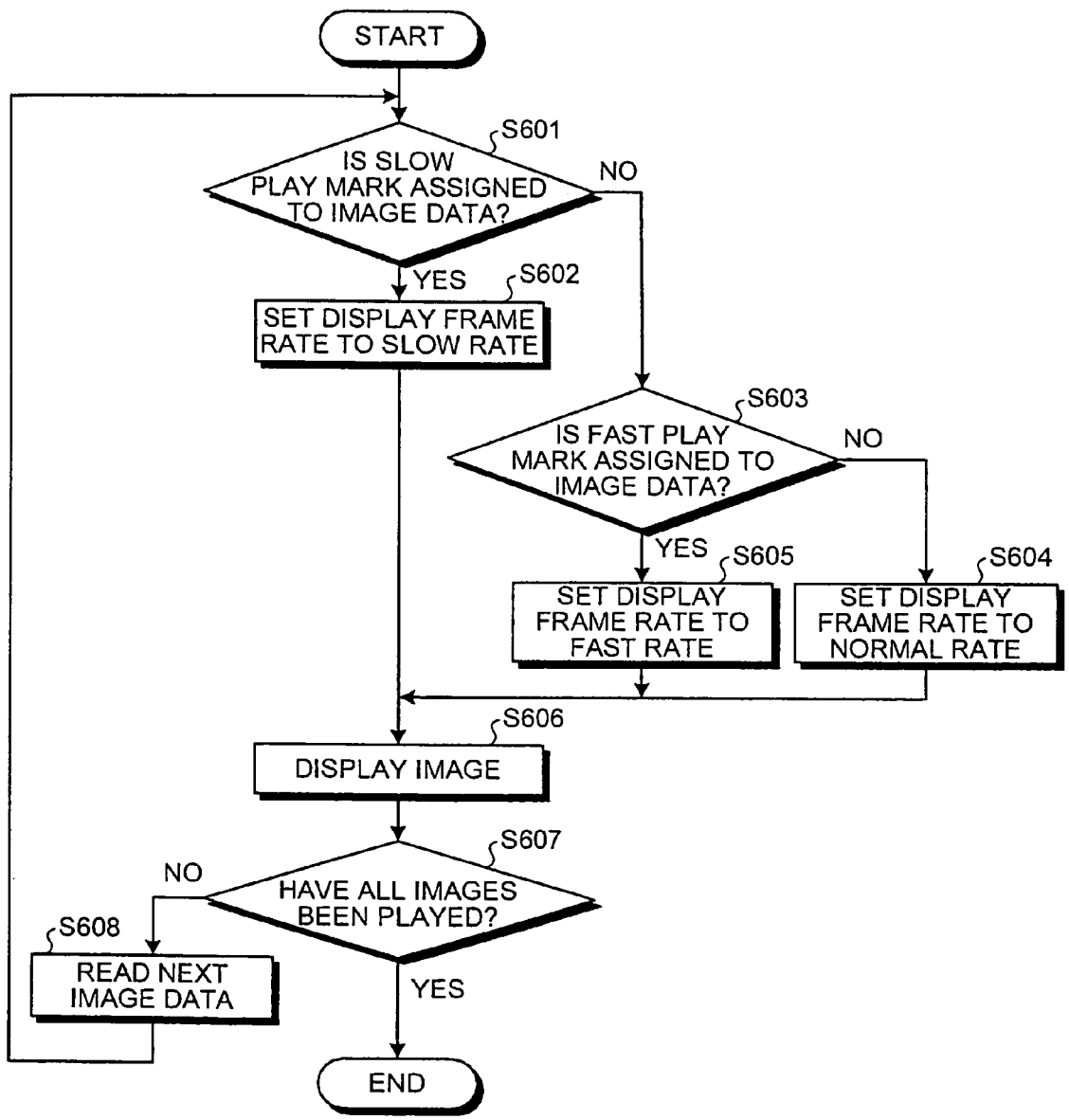
FIG. 14 is a flowchart for explaining processing procedures for sequentially displaying images corresponding to a series of image data for which the play region is alternatively designated.
Figure 15:
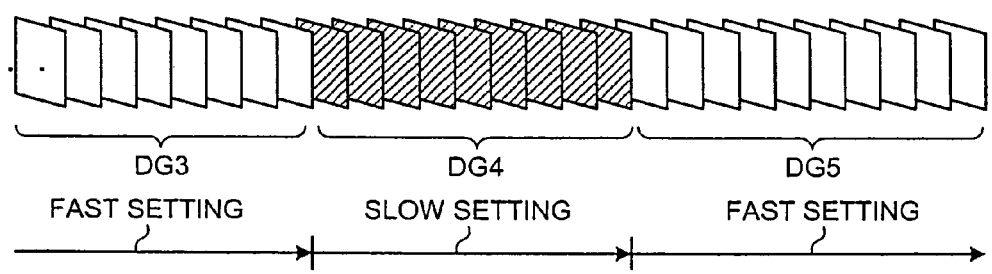
FIG. 15 is a pattern diagram for explaining an operation for setting a display frame rate for each of the series of image data to slow rate or fast rate to correspond to whether the region of the image data is the play region.

FIG. 14 is a flowchart for explaining processing procedures for sequentially displaying images corresponding to a series of image data for which a play region is alternatively selected or images corresponding to a series of image data for which the play region is not designated. FIG. 15 is a pattern diagram for explaining an operation for setting a display frame rate for each of the series of image data to the slow rate or the fast rate to correspond to whether the region of the image data is the play region. Referring to FIG. 14, the control unit 32 determines, similarly to the step S201, whether the slow play mark is assigned to read one-frame image data (step S601). If the control unit 32 determines that the slow play mark is assigned to the image data (step S601, Yes), the frame rate controller 32b changes the display frame rate for the image data, to which the slow play mark is assigned, to the slow display frame rate similarly to the step S203 (step S602).

If the control unit 32 determines that the slow play mark is not assigned to the image data (step S601, No), the control unit 32 determines whether the fast play mark is assigned to the image data (step S603). If the control unit 32 determines that the fast play mark is not assigned to the image data (step S603, No), the frame rate controller 32b sets the display frame rate for the image data, to which neither the slow play mark nor the fast play mark are assigned, to the normal display frame rate (step S604). It is to be noted that the step S604 is executed only when images corresponding to a series of image data for which the play region is not selected (that is, a series of image data for which the designated play region is not discriminated from the other regions) are to be displayed.

If the control unit 32 determines that the fast play mark is assigned to the image data (step S603, Yes), the frame rate controller 32b changes the display frame rate for the image data, to which the fast play mark is assigned, from the normal rate to the fast rate (step S605). Namely, the frame rate controller 32b decides that the display frame rate for the image data, to which the fast play mark is assigned, is set to the fast display frame rate.

As shown in FIG. 15, for example, the frame rate controller 32b changes the display frame rate for each of image data, to each of which data the fast play mark is assigned, in the image data group DG3 on regions other than the play region among the series of image data on the subject 1 to the fast rate, changes the display frame rate for each of image data, to each of which data the slow play mark is assigned, in the image data group DG4 on the play region to the slow rate, and sets the display frame rate for each of image data, to each of which data the fast play mark is assigned, in the image data group DG5 to the fast rate.

If the frame rate controller 32b decides that the display frame rate for the image data is set to the slow rate, the fast rate or the normal rate, the control unit 32 controls the display unit 12 to display the image of the subject 1 corresponding to the image data at the display frame rate decided by the frame rate controller 32b (step S606). In this case, if image data to which the fast play mark is assigned (e.g., each of the image data in the image data groups DG3 and DG5 other than the image data on the play region) is to be displayed in the main-image display area A1, the control unit 32 controls the display unit 12 to display the image forcedly at the fast display frame rate, irrespectively of the image-display instruction information input from the input unit 11. Furthermore, if image data to which the slow play mark is assigned (e.g., each of the image data in the image data group DG4 on the play region) is to be displayed in the main-image display area A1, the control unit 32 controls the display unit 12 to display the image forcedly at the slow display frame rate, irrespectively of the image-display instruction information input from the input unit 11.

Thereafter, the control unit 32 determines whether all of the series of images of the subject 1 have been played similarly to the step S205. If determining that all of the series of images of the subject 1 have not been played yet, then the control unit 32 reads temporally-continuous next data and repeats the processing at and after the step S601 similarly to the step S206 (steps S607 and S608). The control unit 32 can thereby sequentially display images corresponding to all the image data on the selected play region (e.g., all the image data in the image data group DG4) among the series of image data for which the play region is alternatively designated, at the slower display frame rate than the normally-set display frame rate, and sequentially display images corresponding to all the image data on the regions other than the play region (e.g., all the image data in the image data groups DG3 and DG5) at the faster display frame rate than that for displaying the images corresponding to the image data on the play region. Namely, the image corresponding to the image data to which the slow play mark is assigned (e.g., the image data on the play region) is displayed for longer time than the time for displaying the images corresponding to the other image data, thus facilitating examiner's observation. Moreover, the image corresponding to the image data, to which the fast play mark is assigned, is displayed for shorter time than the time for displaying the images corresponding to the other image data, thus shortening time for observing the image data. It is to be noted that the control unit 32 can sequentially display images corresponding to all the series of image data, for which the play region is not designated, at the normally-set display frame rate.

In the third embodiment of the present invention, the images of the regions other than the play region among the series of images for which the play region is alternatively designated are displayed at the fast display frame rate. However, the present invention is not limited thereto. The images of the regions other than the play region can be deleted, i.e., cut from the series of display-target images. In this alternative, the image extracting unit 32a performs a processing for assigning a skip mark to each of the image data on the regions other than the play region in place of the processing at the step S509, at the steps S501 to S510. The control unit 32 can thereby acquire the series of image data on the subject 1 constituted by the all the image data on the play region, to each of which data the slow play mark is assigned, and all the image data on the regions other than the play region, to each of which data the skip mark is assigned. It is to be noted that the skip mark is a flag assigned to image data, the image corresponding to which is to be cut, among the series of image data the images corresponding to which are to be displayed.

Figure 16:
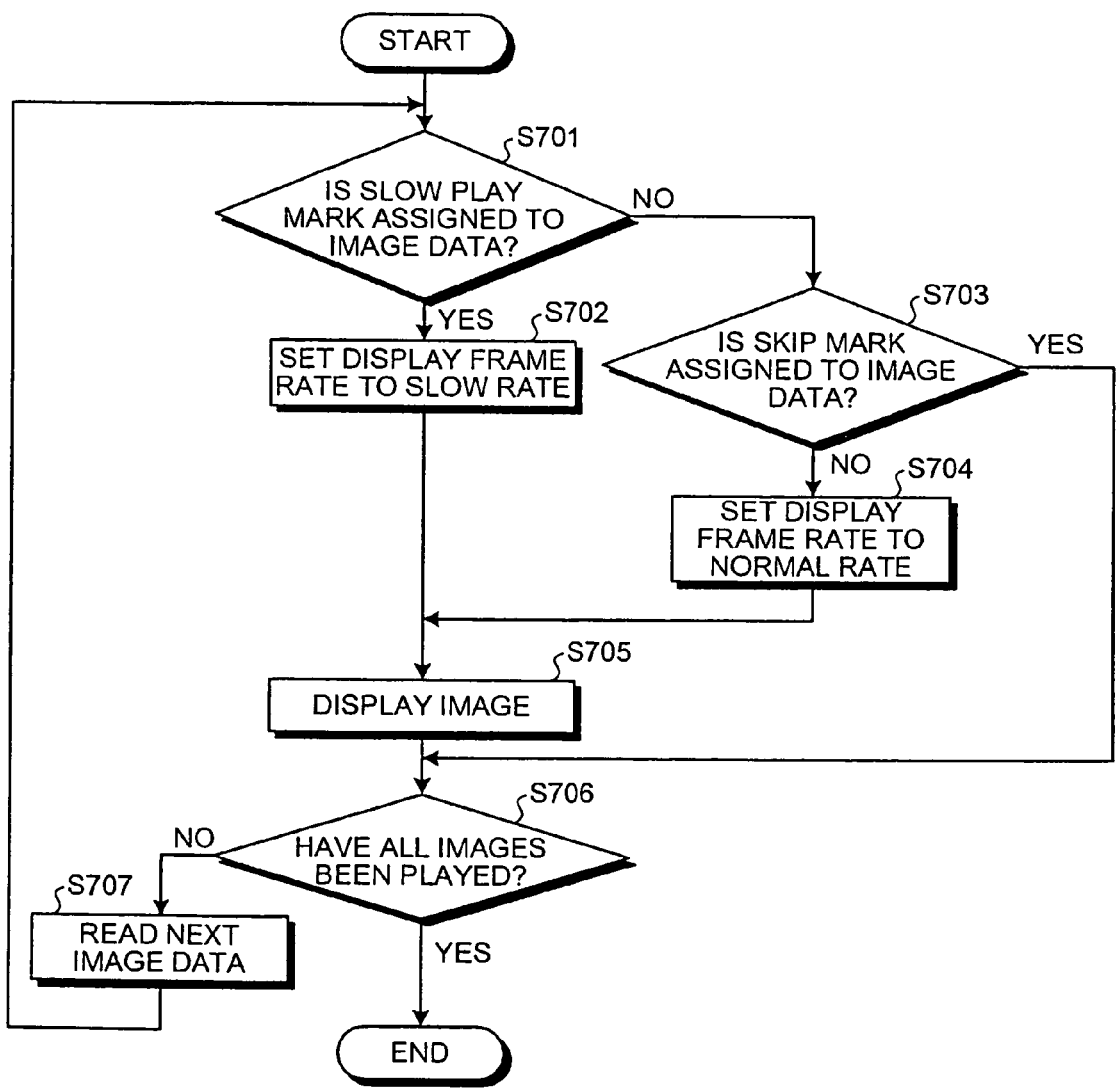
FIG. 16 is a flowchart for explaining a modification of processing procedures for sequentially displaying images corresponding to the series of image data for which the play region is alternatively selected.
Figure 17:
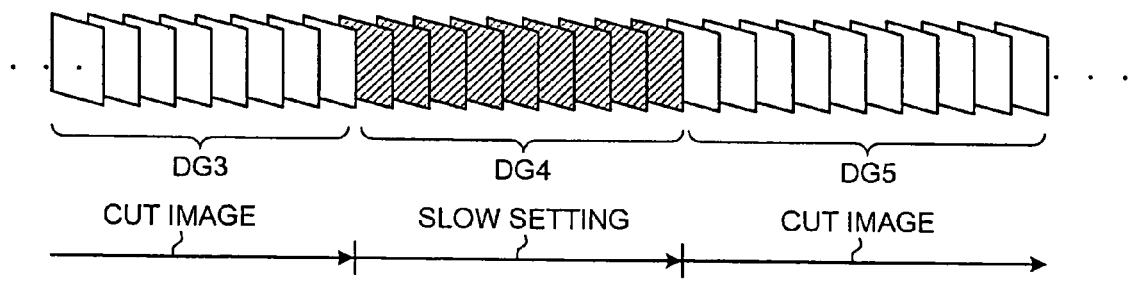
FIG. 17 is a pattern diagram for explaining an operation for setting a display frame rate for the image data on the play region to slow rate and for deleting image data other than the image data on the play region.

FIG. 16 is a flowchart for explaining a modification of processing procedures for sequentially displaying images corresponding to a series of image data for which a play region is alternatively designated or images corresponding to a series of image data for which the play region is not designated. FIG. 17 is a pattern diagram for explaining an operation for setting a display frame rate for each of the image data on the play region to the slow rate, and for deleting image data other than the image data on the play region. Referring to FIG. 16, the control unit 32 performs the same processing as that at the step S601, and the frame rate controller 32b changes the display frame rate, for each of image data to which the slow play mark is assigned, to the slow display frame rate similarly to the step S602 (steps S701 and S702). Furthermore, if the control unit 32 determines that the slow play mark is not assigned to the image data (step S701, No), the control unit 32 determines whether a skip mark is assigned to the image data (step S703). If the skip mark is not assigned to the image data (step S703, No), the frame rate controller 32b sets the display frame rate for the image data to the normal rate (step S704).

Thereafter, the control unit 32 performs the processing almost similarly to that at the steps S606 to S608, and controls the display unit 12 to sequentially display images corresponding to the image data at display frame rates decided by the frame rate controller 32b (steps S705 to S707). On the other hand, if the control unit 32 determines that the skip mark is assigned to the image data (step S703, Yes), the frame rate controller 32b performs a processing for deleting the image data, to which the skip mark is assigned, from a series of image data the images corresponding to which are to be displayed. In the processing for deleting the image data, the frame rate controller 32b can delete the image data, to which the skip mark is assigned, so as to thin out the image data at intervals of a predetermined number of frames among the series of display-target image data, or exclude all image data, to each of which the skip mark is assigned, from the display targets. The control unit 32 performs the processing at and after the step S706 without performing the processing for causing the display unit 12 to display an image (step S705) based on the processing for deleting the image data.

As shown in FIG. 17, for example, the frame rate controller 32b performs a processing for excluding image data in the image data group DG3 on the regions other than the play region, to each of which data the skip mark is assigned, from the image display targets among the series of image data on the subject 1, changes the display frame rate for each of the image data in the image data group DG4 on the play region, to each of which data the slow play mark is assigned, to the slow rate, and a processing for excluding the image data in the image data group DG5 on the regions other than the play region, to each of which data the skip mark is assigned, from the image display targets. In this case, the control unit 32 causes the display unit 12 forcedly not to display all the image data (that is, to cut the images corresponding to all the image data) (e.g., the image data groups DG3 and DG5 on the regions other than the play region), to each of which data the skip mark is assigned, irrespectively of the image-display instruction information input from the input unit 11. Furthermore, as described above, if an image for the image data to which the slow play mark is assigned (e.g., each of the image data in the image data group DG4 on the play region) is to be displayed in the main-image display area A1, the control unit 32 controls the display unit 12 to display the image forcedly at the slow display frame rate, irrespectively of the image-display instruction information input from the input unit 11.

Moreover, in the third embodiment of the present invention, the play region that is the region of interest the images of which are to be displayed is selected, and the images of the selected play region are displayed at the slow display frame rate. However, the present invention is not limited thereto. Regions of no interest for examination can be selected from among the options of the regions in the body of the subject, and images of the selected regions can be displayed at faster display frame rate than that for displaying the images of the region of interest, or the images of the selected regions can be excluded from the display targets.

As described so far, according to the third embodiment of the present invention, besides the functions and the configuration of the second embodiment, the image display apparatus is configured to automatically change the display frame rate for each of the images of the regions other than the selected play region to the fast rate, and to display the images of the selected play region forcedly at the slower display frame rate and the images of the regions other than the play region at the fast rate if the image display apparatus is to sequentially display a series of images of the subject. It is, therefore, possible to realize the image display apparatus that can exhibit the functions and advantages of the second embodiment, that can easily shorten time for sequentially displaying the images of the regions other than the region of interest, i.e., the images of the regions other than the observation target region, and that can further shorten the time for observing the series of images of the subject without hampering observation of the images of the selected, desired region of interest.

Moreover, the image display apparatus is configured to automatically delete the images of the regions other than the selected play region from a series of display-target images, and to display the images of the selected play region forcedly at the slower rate and not to display, i.e., to cut the images of the regions other than the play region if the image display apparatus is to sequentially display a series of images of the subject. It is, therefore, possible to realize the image display apparatus that can easily cut the images of the regions other than the region of interest, i.e., the images of the regions other than the observation target region if a series of images of the subject are to be displayed, that can thereby display images starting at the images of the selected, desired region of interest, that can exhibit the functions and advantages of the second embodiment, and that can further shorten the time for observing the series of images of the subject.

Fourth Embodiment

A fourth embodiment of the present invention will be described. In the third embodiment, the images of the selected play region are displayed at the slow rate and the images of the regions other than the play region are displayed at the fast rate among the series of images of the subject. According to the fourth embodiment, only the images of the selected play region are displayed, and among the images of the play region, those of the bleeding site are displayed at slow rate and those of parts other than the bleeding site are displayed at fast rate.

Figure 18:
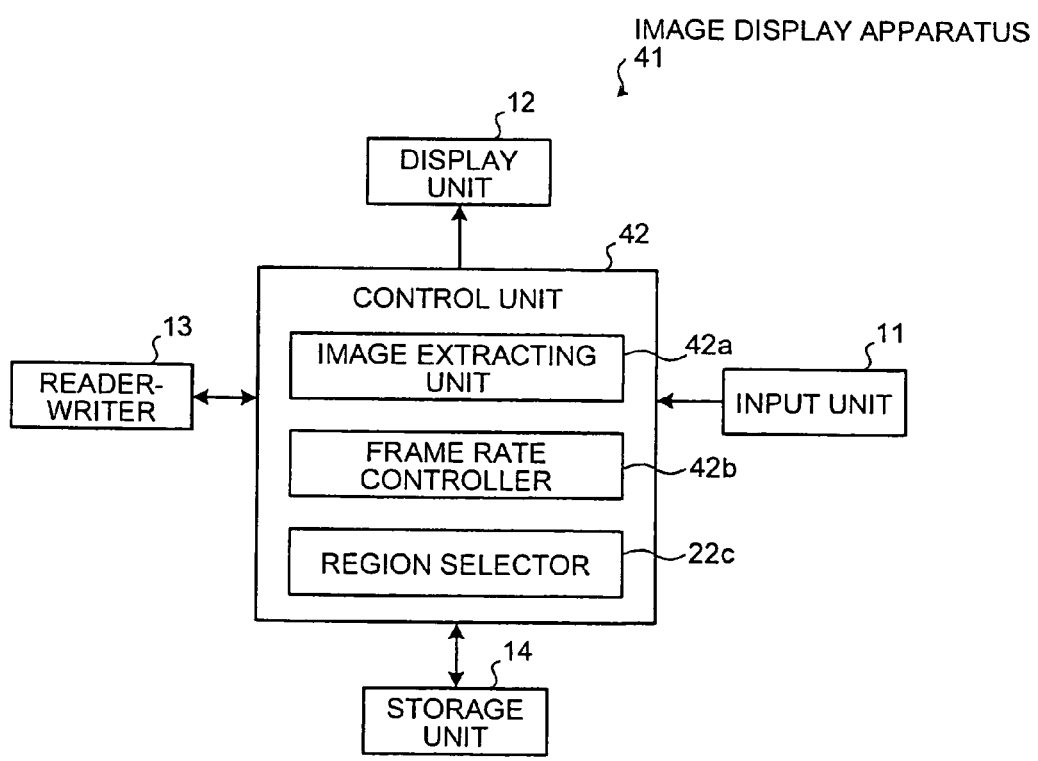
FIG. 18 is a block diagram typically showing an example of a configuration of an image display apparatus according to a fourth embodiment of the present invention.

FIG. 18 is a block diagram typically showing an example of a configuration of an image display apparatus according to the fourth embodiment of the present invention. An image display apparatus 41 includes a control unit 42 in place of the control unit 32 of the image display apparatus 31 according to the third embodiment. The control unit 42 includes an image extracting unit 42a in place of the image extracting unit 32a according to the third embodiment, and a frame rate controller 42b in place of the frame rate controller 32b. The other constituent elements are the same as those according to the third embodiment, and the same constituent elements are denoted by the same reference symbols, respectively.

The control unit 42, which functions almost similarly to the control unit 32, includes the image extracting unit 42a, the frame rate controller 42b, and the region selector 22c. The image extracting unit 42a, which functions almost similarly to the image extracting unit 32a, assigns a slow play mark to each of image data on the bleeding site among the image data on the play region selected by the region selector 22c, and assigns a fast play mark to each of image data on parts of the region other than the bleeding site. Moreover, the image extracting unit 42a assigns a skip mark to each of the image data other than the image data on the selected play region. The frame rate controller 42b, which functions almost similarly to the frame rate controller 32b, includes a function of changing the display frame rate for the image data, to which the fast play mark is assigned, to the fast display frame rate, and performing a processing for deleting the image data, to which the skip mark is assigned, from a series of image-display target image data.

Figure 19:
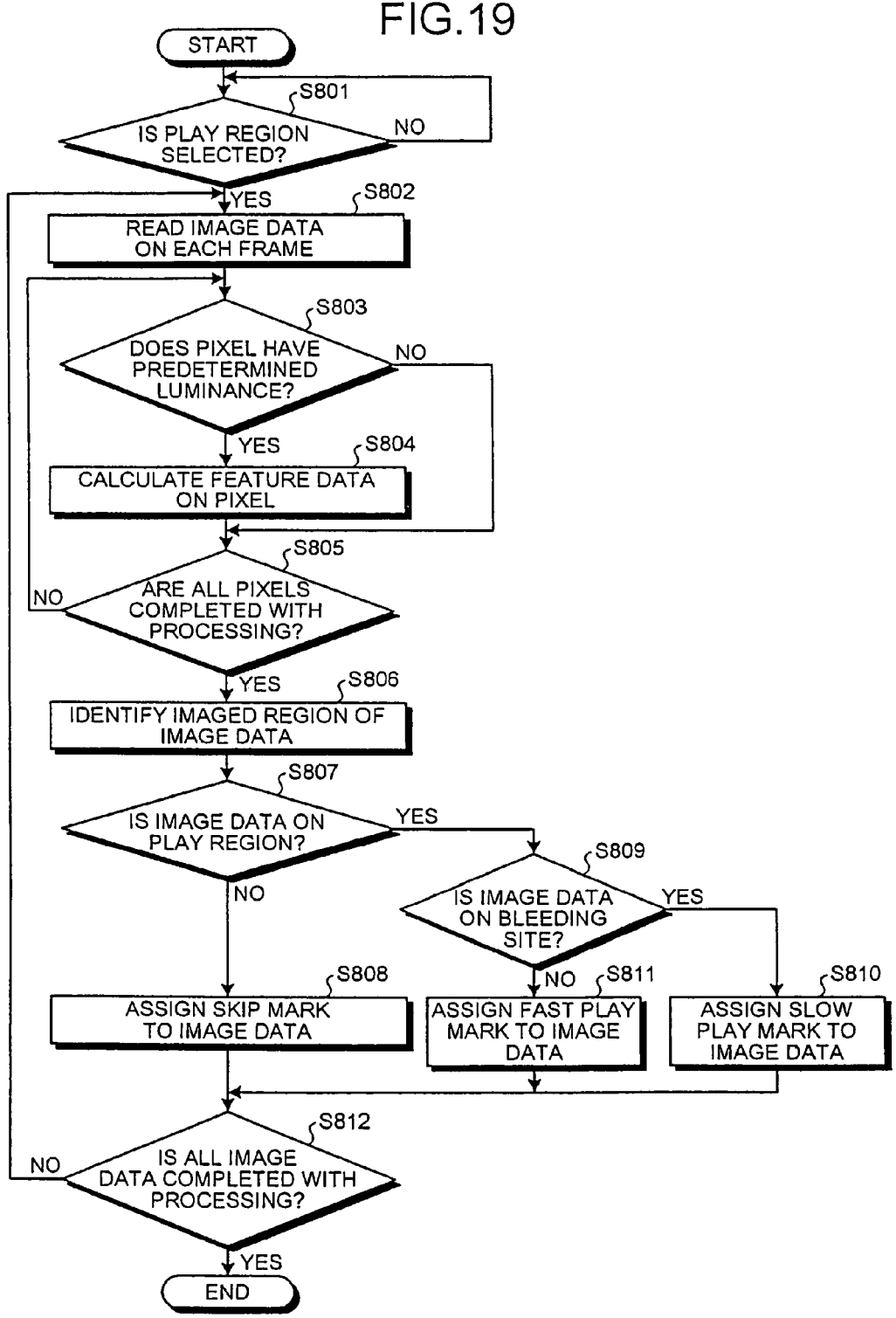
FIG. 19 is a flowchart for explaining processing procedures for assigning a slow play mark, a fast play mark or a skip mark to each of a series of image data.

FIG. 19 is a flowchart for explaining processing procedures for assigning a slow play mark, a fast play mark or a skip mark to each of the series of image data for which a play region is selected. If a play region is selected for the series of image data on the subject 1, the image extracting unit 42a assigns the skip mark to each of all the image data on the regions other than the play region among the series of image data for which the play region is selected. Furthermore, the image extracting unit 42a assigns the slow play mark to all the image data on the bleeding site and the fast play mark to each of all the image data on the parts of the play region other than the bleeding site among all the image data on the play region. Namely, in FIG. 19, the control unit 42 and the image extracting unit 42a perform the same processing as that at the steps S501 to S507, identify an imaged region of each of the image data, and determine whether the image data, the imaged region of which has been identified, is image data on the play region (steps S801 to S807).

Next, if determining that the image data, the imaged region of which has been identified, is image data on the region other than the play region (step S807, No), the image extracting unit 42a assigns the skip mark to the image data on the region other than the play region (step S808). If determining that the image data, the imaged region of which has been identified, is the image data on the play region (step S807, Yes), and determining that the image data on the play region is image data on the bleeding site (step S809, Yes), the image extracting unit 42a assigns the slow play mark to the image data on the bleeding site (step S810). If determining that the image data on the play region is image data on the part of the play region other than the bleeding site (step S809, No), the image extracting unit 42a assigns the fast play mark to the image data on the part of the play region other than the bleeding site (step S811).

Thereafter, the control unit 42 performs the same processing as that at the step S510 (step S712), and repeats the processing at the steps S801 to S812 on all of the series of image data on the subject 1. The control unit 42 can thereby acquire the series of image data constituted by the image data on the regions other than the play region, to each of which data the skip mark is assigned, and the image data on the play region, to each of which data either the slow play mark or fast play mark is assigned. The image data on the play region is constituted by the image data on the bleeding site, to each of which data the slow play mark is assigned, and the image data on the parts of the play region other than the bleeding site, to each of which data the fast play mark is assigned.

Figure 20:
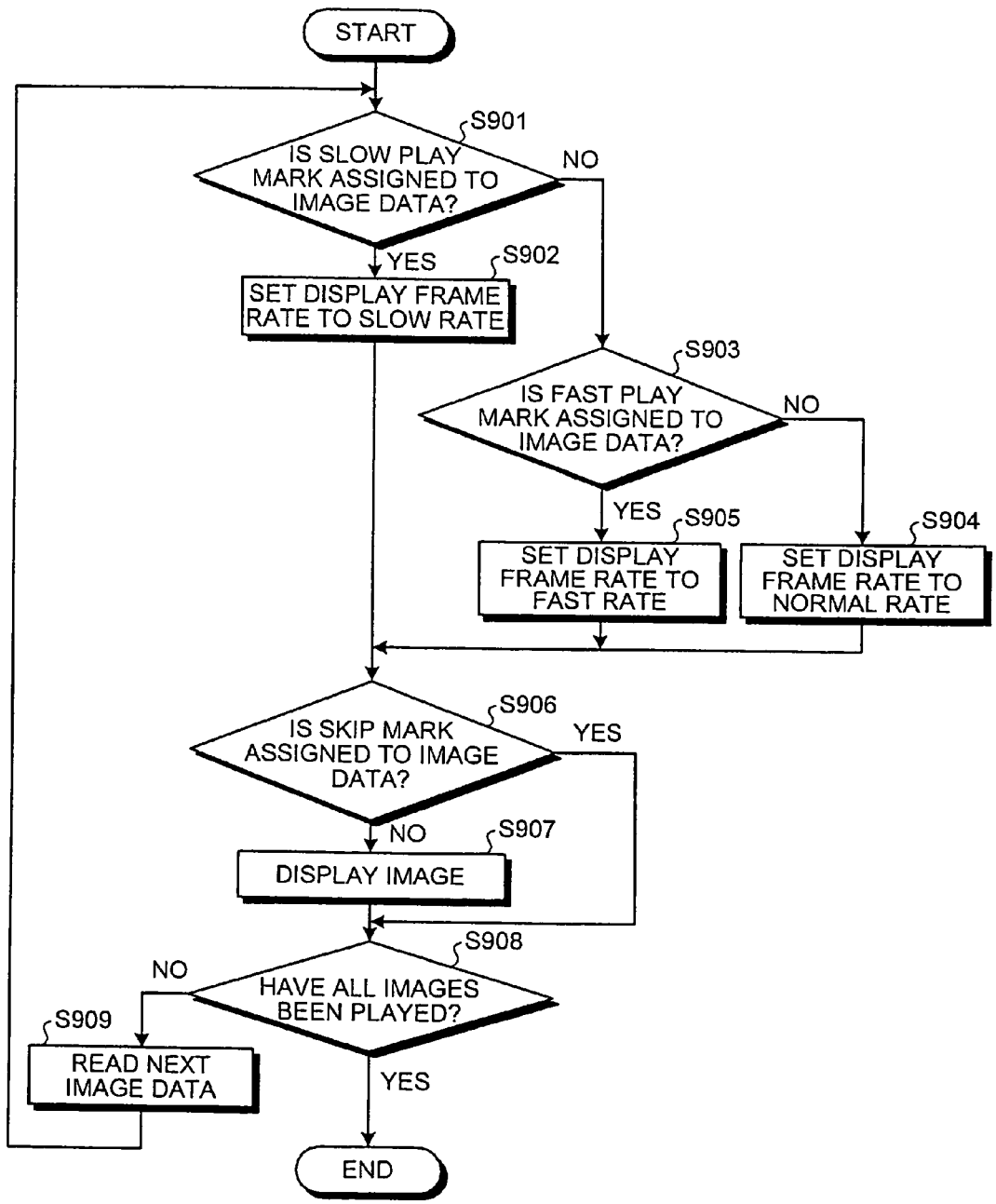
FIG. 20 is a flowchart for explaining processing procedures for sequentially displaying images corresponding to a series of image data for which a play region is alternatively selected.
Figure 21:
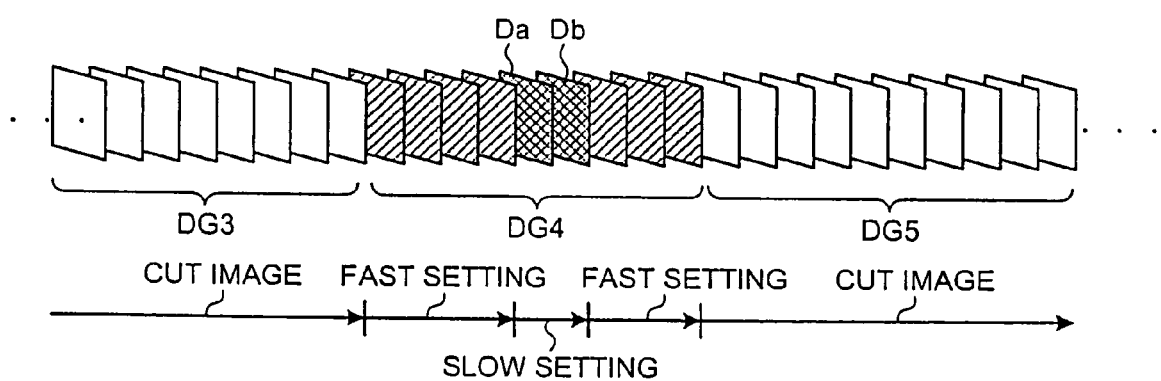
FIG. 21 is a pattern diagram for explaining an operation for setting a display frame rate for each of the image data on the play region to slow rate or fast rate and for deleting image data other than the image data on the play region.

FIG. 20 is a flowchart for explaining processing procedures for sequentially displaying images corresponding to a series of image data for which a play region is alternatively designated or images corresponding to a series of image data for which the play region is not designated. FIG. 21 is a pattern diagram for explaining an operation for setting a display frame rate for each of the image data on the play region to the slow or fast rate, and for deleting the image data on the regions other than the play region. Referring to FIG. 20, the control unit 42 and the frame rate controller 42b perform the processing similarly to that at the steps S601 to S605 (steps S901 to S905). In this case, the frame rate controller 42b sets the display frame rate for the image data, to which neither the slow play mark nor the fast play mark are assigned, among the series of image data on the subject 1 to the normal rate (step S904), changes the display frame rate for the image data, to which the slow play mark is assigned, from the normal rate to the slow rate (step S902), and changes the display frame rate for the image data, to which the fast display mark is assigned, from the normal rate to the fast display frame rate (step S905).

Next, the control unit 42 determines whether the skip mark is assigned to the image data at the display frame rate set to the slow rate, the fast rate or the normal rate (step S906). If determining that the skip mark is not assigned to the image data (step S906, No), the control unit 42 controls the display unit 12 to display an image of the subject 1 corresponding to the image data at the display frame rate decided by the frame rate controller 42b (step S907). If determining that the skip mark is assigned to the image data (step S906, Yes), the frame rate controller 42b performs a processing for deleting the image data from the series of image data the images corresponding to which are to be displayed. The control unit 42 causes the display unit 12 not to display the image data based on the processing.

As shown in FIG. 21, for example, the frame rate controller 42b performs a processing for deleting image data in the image data groups DG3 and DG5 on the regions other than the play region, to each of which data the skip mark is assigned, from the image display targets among the series of image data on the subject 1. Furthermore, the frame rate controller 42b changes the display frame rate for each of image data Da and Db on the bleeding site, to each of which data the slow play mark is assigned, among the image data in the image data group DG4 on the play region to the slow rate, and changes the display frame rate for each of the image data on the play region, to each of which data the fast play mark is assigned, that is, the display frame rate for each of the image data on the parts of the play region other than the bleeding site to the fast rate. In this case, the control unit 42 causes the display unit 12 forcedly not to display all the image data to each of which data the skip mark is assigned (that is, cuts the images) (e.g., the image data groups DG3 and DG5 on the regions other than the play region), irrespectively of the image-display instruction information input from the input unit 11. Furthermore, if images corresponding to the image data on the play region (e.g., the respective image data in the image data group DG4 on the play region) are to be displayed in the main-image display area A1, the control unit 42 controls the display unit 12 to display the images corresponding to the image data on the bleeding site among the image data on the play region (e.g., the image data Da and Db) at the slow display frame rate, and controls the image data on the parts of the play region other than the bleeding site (e.g., the image data in the image data group DG4 except for the image data Da and Db) at the fast display frame rate.

Thereafter, the control unit 42 determines whether all the images of the subject 1 have been played similarly to the step S607. If determining that all the images of the subject 1 have not been played yet, the control unit 42 reads temporally-continuous next data and performs the processing at and after the step S901 similarly to the step S608 (steps S908 and S909). The control unit 42 can thereby delete the image data to each of which data the skip mark is assigned, that is, the image data on the regions other than the play region among the series of image data on the subject 1 from the series of image data, sequentially display images corresponding to the image data, to each of which data the slow play mark is assigned, that is, the image data on the bleeding site among that on the play region at the slow rate, and sequentially display images corresponding to the image data to each of which data the fast play mark is assigned, that is, the image data on the parts of the play region except for the bleeding site at the fast rate. This enables only the images of the desired organ selected by the examiner, e.g., one of the esophagus, the stomach, the small intestine, and the large intestine to be displayed to thereby shorten the time for observing a series of images, and the images of the bleeding site among those of the desired organ to be displayed at the slower rate than the rate for displaying the images of the parts of the play region other than the bleeding site (that is, to be displayed for longer time), and facilitates observation of the bleeding site of the desired organ.

In the fourth embodiment of the present invention, the images corresponding to the image data on the bleeding site among the image data on the play region are displayed at the slow rate. However, the present invention is not limited thereto. Images corresponding to image data on a lesion site such as a tumor among the image data on the play region can be displayed at the slow rate. Alternatively, images corresponding to the image data obtained by imaging at least one of the bleeding site and the lesion site can be displayed at the slow rate.

As described so far, according to the fourth embodiment of the present invention, besides the functions and the configuration of the third embodiment, the image display apparatus is configured not to display, i.e., to cut the images on the regions other than the selected play region among the series of sequentially displayed images, to display the images of the medically abnormal site such as the bleeding site or the lesion site among the images of the play region at the slow rate, and to display the images of the play region except for the medically abnormal site at the fast rate. It is, therefore, possible to realize the image display apparatus that can easily cut images other than those of the observation target region and that can display the medically abnormal site among the images of the observation target region forcedly at the slow rate if the image display apparatus is to display the series of images of the subject, that can exhibit the functions and advantages of the third embodiment, and that can easily observe the abnormal site in the organ designated as the observation target.

By using the image display apparatus according to the present invention, the examiner can automatically display only the images of the organ, e.g., the small intestine, designated as the observation target among the series of images of the subject, and can automatically display the images of the medically abnormal site such as the bleeding site or the lesion site among the images of the designated organ, e.g., the small intestine, at the slow rate. The examiner can thereby easily observe the medically abnormal site, and observe the organ designated as the observation target using a pseudo moving image. This is useful when the examiner examines a state of the organ in the body of the subject.

INDUSTRIAL APPLICABILITY

As described so far, the image display apparatus according to the present invention is suitable for the image display apparatus that can display a series of images obtained by imaging the interior of the digestive lumen of the subject, and that can shorten the time for observing the series of intra-subject images without hampering observation of the desired observation target region or the medically abnormal site.

The invention claimed is:

1. An image display apparatus for displaying a series of images of an interior of a subject picked up along time series, comprising:
   an image extracting unit that extracts at least one of the series of images having a feature of a region of interest, and identifies the at least one of the series of images as an image of the region of interest of the interior of the subject;
   an input unit that receives a display frame rate for the series of images;
   a frame-rate controller that sets the display frame rate received by the input unit for the series of images, changes the display frame rate for the at least one of the series of images to first display frame rate that is slower than the received display frame rate, and changes the display frame rate for the rest of the series of images to a second display frame rate that is faster than the received display frame rate; and
   a controller that controls to display the series of images at the first display frame rate and the second display frame rate.

2. The image display apparatus according to claim 1, wherein the frame rate controller sets the first display frame rate to be slower than the second display frame rate.

3. The image display apparatus according to claim 1, wherein the frame rate controller excludes the rest of the series of images.

4. The image display apparatus according to claim 1, further comprising a region selector that selects a play region including the region of interest for the interior of the subject, wherein
   the image extracting unit extracts at least one of the series of images having a feature of the selected play region, and identifies the at least one of the series of images thus extracted as the image of the region of interest.

5. The image display apparatus according to claim 4, wherein the image extracting unit further extracts at least one of the series of images having a feature of a medically abnormal site from the at least one of the series of images having the feature of the selected play region, and identifies the at least one of the series of images thus extracted as an image of the abnormal site, and the frame rate controller deletes the rest of the series of images and sets a third display frame rate for the at least one of the series of images extracted as the image of the abnormal site, the third display frame rate being slower than the first display frame rate.

6. The image display apparatus according to claim 4, wherein the selected play region is one of an esophagus, a stomach, a small intestine, a large intestine, and a bleeding site in the interior of the subject.

7. The image display apparatus according to claim 1, wherein the region of interest is a medically abnormal site.

8. The image display apparatus according to claim 7, wherein the medically abnormal site is a bleeding site or a lesion site.

9. An image display apparatus for displaying a series of images of an interior of a subject picked up along time series, comprising:
   an input unit that receives a display frame rate for the series of images, and
   a controller including:
      an image extracting unit that extracts at least one of the series of images having a feature of a region of interest, identifies the at least one of the series of images as an image of the region of interest of the interior of the subject, and assigns a slow play mark to the at least one of the series of images identified as the image of the region of interest; and
      a frame-rate controller that sets the display frame rate received by the input unit for the series of images, changes the display frame rate of the at least one of the series of images to be slower than the received display frame rate, and changes the display frame of the rest of the series of images to be faster than the received display frame rate, wherein
   the controller sequentially displays the series of images at the display frame rates set by the frame-rate controller.

10. The image display apparatus according to claim 9, wherein the frame rate controller excludes the rest of the series of images.

11. The image display apparatus according to claim 9, further comprising a region selector that selects a play region including the region of interest for the interior of the subject, wherein,
   the image extracting unit extracts at least one of the series of images having a feature of the selected play region, and identifies the at least one of the series of images thus extracted as the image of the region of interest.

12. The image display apparatus according to claim 11, wherein the image extracting unit further extracts at least one of the series of images having a feature of a medically abnormal site from the at least one of the series of images having the feature of the selected play region, and identifies the at least one of the series of images thus extracted as an image of the abnormal site, and the frame rate controller deletes the rest of the series of images to which the slow play mark is not assigned and sets a display frame rate for the at least one of the series of images extracted as the image of the abnormal site to be slower than the display frame rate of the image to which the slow play mark is assigned.

13. The image display apparatus according to claim 11, wherein
   the image extracting unit assigns a skip mark to the rest of the series of images to which the slow play mark is not assigned, and
   the controller skips displaying the rest of the series of images to which the skip mark is assigned.

14. The image display apparatus according to claim 11, wherein the selected play region is one of an esophagus, a stomach, a small intestine, a large intestine, and a bleeding site in the interior of the subject.

15. The image display apparatus according to claim 9, wherein the image extracting unit assigns the slow play mark to at least one of an image temporally prior to the at least one of the series of images to which the slow play mark is assigned and an image temporally after the at least one of the series of images to which the slow play mark is assigned.

16. The image display apparatus according to claim 9, wherein the region of interest is a medically abnormal site.

17. The image display apparatus according to claim 16, wherein the medically abnormal site is a bleeding site or a lesion site.

18. An image display apparatus for displaying a series of images of an interior of a subject picked up along time series, comprising:
   an input unit that receives a display frame rate for the series of images;
   a region selector that selects a play region for the interior of the subject;
   an image extracting unit that extracts at least one of the series of images having a feature of the selected play region, assigns a slow play mark to at least one of the series of images thus extracted corresponding to at least one of a bleeding site and a lesion site, assigns a fast play mark faster than the slow play mark to rest of the at least one of the series of images thus extracted not corresponding to the at least one of the bleeding site and the lesion site, and assigns a skip mark to rest of the series of images not extracted,
   the frame-rate controller sets the display frame rate received by the input unit for the series of images, changes the display frame rate for the at least one of the series of images to which the slow play mark is assigned to a slow display frame rate that is slower than the received display frame rate, and changes the display frame rate for the rest of the at least one of the series of images to which the fast mark is assigned to a fast display frame rate that is faster than the received display frame rate, and,
   when the series of images are sequentially displayed, the controller controls to display the at least one of the series of images to which the slow play mark is assigned at the slow display frame rate, display the rest of the at least one of the series of images to which the fast play mark is assigned at the fast display rate frame rate, and to skip displaying the rest of the series of images to which the skip mark is assigned.

* * * * *